US012789486B2

(12) United States Patent
Newman

(10) Patent No.: US 12,789,486 B2
(45) Date of Patent: Nov. 10, 2026

(54) APPARATUS AND METHODS FOR CONTROLLING AXIAL GROWTH WITH AN OCULAR LENS

(71) Applicant: MENICON SINGAPORE PTE LTD., Singapore (SG)

(72) Inventor: Stephen D. Newman, Singapore (SG)

(73) Assignee: MENICON SINGAPORE PTE. LTD., Singapore (SG)

( * ) Notice: Subject to any disclaimer, the term of this patent is extended or adjusted under 35 U.S.C. 154(b) by 241 days.

(21) Appl. No.: 18/604,160

(22) Filed: Mar. 13, 2024

(65) Prior Publication Data

US 2024/0408834 A1 Dec. 12, 2024

Related U.S. Application Data

(63) Continuation of application No. 16/535,972, filed on Aug. 8, 2019, now Pat. No. 11,947,194, which is a (Continued)

(30) Foreign Application Priority Data

Mar. 24, 2014 (SG) ........................... 10201400920R

(51) Int. Cl.
*B29D 11/00* (2006.01)
*A61F 2/16* (2006.01)
(Continued)

(52) U.S. Cl.
CPC ...... *B29D 11/00326* (2013.01); *A61F 2/1602* (2013.01); *B29C 33/3842* (2013.01);
(Continued)

(58) Field of Classification Search
CPC .......... B29D 11/0048; B29D 11/00144; B29D 11/00125; B29D 11/0073;
(Continued)

(56) References Cited

U.S. PATENT DOCUMENTS 6,120,148 A 9/2000 Fiala et al.
2002/0034710 A1 3/2002 Morris et al.
(Continued)

FOREIGN PATENT DOCUMENTS

CN 101467092 A 6/2009
EP 2412767 A1 2/2012
(Continued)

OTHER PUBLICATIONS

Extended European Search Report for European Patent Application No. 15768866.4, dated Mar. 26, 2018 (19 pages).
(Continued)

*Primary Examiner* — Mathieu D Vargot
(74) *Attorney, Agent, or Firm* — Dorsey & Whitney LLP

(57) ABSTRACT

One embodiment of an ocular lens includes a lens body configured to contact an eye where the lens body has an optic zone shaped to direct central light towards a central focal point of a central region of a retina of the eye. At least one optic feature of the lens body has a characteristic that directs peripheral light off axis into the eye away from the central region of the retina. Another embodiment of an ocular lens has at least one isolated feature of the lens body that has a characteristic of directing peripheral light off axis into the eye away from the central region of the retina. Methods of making contact lenses include forming the features during the manufacturing process.

21 Claims, 15 Drawing Sheets

Related U.S. Application Data continuation of application No. 15/127,532, filed as application No. PCT/SG2015/050050 on Mar. 24, 2015, now Pat. No. 10,429,670.

(51) Int. Cl.

| | |
|---|---|
| ***B29C 33/38*** | (2006.01) |
| ***B33Y 10/00*** | (2015.01) |
| ***G02C 7/04*** | (2006.01) |
| *B29K 83/00* | (2006.01) |
| *B29K 105/00* | (2006.01) |
| *B29L 11/00* | (2006.01) |
| *B29L 31/00* | (2006.01) |
| *B33Y 80/00* | (2015.01) |

(52) U.S. Cl.

CPC .. *B29D 11/00115* (2013.01); *B29D 11/00317* (2013.01); *B33Y 10/00* (2014.12); *G02C 7/049* (2013.01); *B29D 11/00125* (2013.01); *B29D 11/00144* (2013.01); *B29D 11/0048* (2013.01); *B29D 11/0073* (2013.01); *B29K 2083/00* (2013.01); *B29K 2105/0061* (2013.01); *B29L 2011/0041* (2013.01); *B29L 2031/757* (2013.01); *B33Y 80/00* (2014.12); *G02C 7/041* (2013.01); *G02C 2202/16* (2013.01); *G02C 2202/20* (2013.01); *G02C 2202/24* (2013.01)

(58) Field of Classification Search

CPC ........ B29D 11/00317; B29D 11/00326; B33Y 10/00; B33Y 80/00; B29C 33/3842

See application file for complete search history.

(56) References Cited

U.S. PATENT DOCUMENTS

| | | | | |
|---|---|---|---|---|
| 2004/0184158 | A1 | 9/2004 | Shadduck | |
| 2005/0046957 | A1 | 3/2005 | Lai et al. | |
| 2005/0182489 | A1 | 8/2005 | Peyman | |
| 2006/0082729 | A1 | 4/2006 | To et al. | |
| 2008/0218687 | A1 | 9/2008 | Phillips | |
| 2008/0231801 | A1* | 9/2008 | Iuliano .................... | G02C 7/02 351/159.73 |
| 2008/0269882 | A1 | 10/2008 | Simpson et al. | |
| 2008/0269885 | A1 | 10/2008 | Simpson et al. | |
| 2008/0269886 | A1 | 10/2008 | Simpson et al. | |
| 2010/0036489 | A1 | 2/2010 | Lindacher et al. | |
| 2011/0040377 | A1 | 2/2011 | Battis et al. | |
| 2011/0051079 | A1 | 3/2011 | Martinez et al. | |
| 2011/0153012 | A1* | 6/2011 | Legerton .................. | G02C 7/04 351/159.23 |
| 2012/0133064 | A1 | 5/2012 | Newman | |
| 2012/0194780 | A1 | 8/2012 | Back | |
| 2013/0010255 | A1 | 1/2013 | Holden et al. | |
| 2013/0293834 | A1 | 11/2013 | Wang | |
| 2014/0052245 | A1 | 2/2014 | Zickler et al. | |
| 2015/0160477 | A1 | 6/2015 | Dai | |
| 2016/0306192 | A1 | 10/2016 | Marshall et al. | |
| 2016/0377884 | A1 | 12/2016 | Lau et al. | |
| 2017/0212277 | A1* | 7/2017 | Chapoy .................. | G02B 1/041 |
| 2018/0017814 | A1 | 1/2018 | Tuan et al. | |

FOREIGN PATENT DOCUMENTS

| | | | |
|---|---|---|---|
| ES | 2421464 | A1 | 9/2013 |
| JP | 2007511803 | A | 5/2007 |
| JP | 2009540373 | A | 11/2009 |
| JP | 2011510798 | A | 4/2011 |
| JP | 2011518355 | A | 6/2011 |
| JP | 2017510851 | A | 4/2017 |
| KR | 101173296 | B1 | 8/2012 |
| TW | I297791 | B | 6/2008 |
| WO | 2005055891 | A1 | 6/2005 |
| WO | 2007146673 | A2 | 12/2007 |
| WO | 2009129528 | A1 | 10/2009 |
| WO | 2013191148 | A1 | 12/2013 |
| WO | 2015147758 | A1 | 10/2015 |

OTHER PUBLICATIONS

First Office Action for Japanese Patent Application No. 2016-559337, dated Sep. 11, 2018, with English translation (7 pages).

First Office Action for Japanese Patent Application No. 2019-153003, dated Nov. 26, 2019, with English translation (12 pages).

PCT International Search Report for PCT International Patent Application No. PCT/SG2015/050050, dated Jun. 30, 2015 (5 pages).

Supplementary Partial European Search Report for corresponding European Patent Application No. EP15768866, mailed Nov. 7, 2017 (4 pages).

Partial European Search Report for EP Application No. 24174525.6, dated Aug. 20, 2024.

* cited by examiner

APPARATUS AND METHODS FOR CONTROLLING AXIAL GROWTH WITH AN OCULAR LENS

CROSS-REFERENCE TO RELATED APPLICATION(S)

This application is a continuation of U.S. patent application Ser. No. 16/535,972, filed Aug. 8, 2019, now U.S. Pat. No. 11,947,194, and entitled "APPARATUS AND METHODS FOR CONTROLLING AXIAL GROWTH WITH AN OCULAR LENS," which is a continuation of U.S. patent application Ser. No. 15/127,532, filed Sep. 20, 2016, now U.S. Pat. No. 10,429,670, and entitled "APPARATUS AND METHODS FOR CONTROLLING AXIAL GROWTH WITH AN OCULAR LENS," which is 371 of International Patent Application No. PCT/SG2015/050050, filed Mar. 24, 2015, and entitled "APPARATUS AND METHODS FOR CONTROLLING AXIAL GROWTH WITH AN OCULAR LENS," which claims priority to Singapore Application No. 10201400920R, filed Mar. 24, 2014, and entitled "APPARATUS AND METHODS FOR CONTROLLING AXIAL GROWTH WITH AN OCULAR LENS," all of which are hereby incorporated by reference in their entireties.

BACKGROUND

Emmetropia is a state of vision where a viewer sees objects clearly at both near and far distances. The cornea and crystalline lens collectively focus the light entering the eye to the central regions of the retina. Emmetropia is achieved when the collective refractive powers of the cornea and crystalline lens focus light exactly onto the central portion of the retina.

Myopia is a vision condition where objects near to a viewer appear clear, but objects that are spaced farther away from the viewer get progressively blurred. Myopia is sometimes referred to as being nearsighted. Myopia can be caused by any number of conditions and reasons. A significant factor for many cases of myopia includes an elongated axial length of the eye. Myopia occurs when the focal point of the focused light entering the eye is formed before the retina. In other words, the focus of the light rays entering the eye converges short of the retina.

Another condition that is affected by the eye's axial length is hyperopia. This condition causes the viewer to see objects at a distance clearly, while the objects close to the viewer are progressively burred. While this condition can occur for multiple reasons as well, a person typically has hyperopia if the focal point of the focused light entering the eye is formed behind the retina.

The axial length of the eye grows as children age. As young people begin their young adulthood years, the eye generally stops growing and the axial length of the eye becomes more permanent. Thus, if the growth of the eye's axial length can be controlled during a child's youth, myopia or hyperopia can be reduced or even eliminated in the child's adulthood years. What is needed is an apparatus, system, and method for controlling the growth of the eye's axial length during any stage of life where the axial length of the eye is capable of growing.

SUMMARY

A number of representative embodiments are provided to illustrate the various features, characteristics, and advantages of the disclosed subject matter. It should be understood that the features, characteristics, advantages, etc., described in connection with one embodiment can be used separately or in various combinations and sub-combinations with other features described in connection with other embodiments.

In one embodiment of the principles described herein, an ocular lens includes a lens body configured to contact an eye. The lens body includes an optic zone configured to direct light towards a central region of the retina of the eye. At least one optic feature of the lens body has a characteristic that selectively directs light into the eye away from the central region of the retina. The ocular lens may be a contact lens, a soft contact lens, a rigid gas permeable contact lens, an implantable lens, or combinations thereof.

In some cases, the optic feature is a printed featured. Such a printed feature can be formed using pad printing processes, plate printing processes, etch printing processes, dot matrix printing processes, laser printing processes, tamp printing processes, liquid jet printing processes, other printing processes, or combinations thereof.

The optic feature can be formed on an anterior surface of the ocular lens. In examples where the lens body is made of multiple layers, the optic feature can be formed on an internal or external surface of any one of the layers. Such an internal or external surface can be on an intermediate layer or on another surface of an anterior layer or a posterior layer.

The optic features may be made of a silicone material, a hydrogel material, an optical material, a colored material, or combinations thereof. The optic features can be formed in any appropriate location on the ocular lens so that the features do not diminish optical clarity of the lens by preventing the central light to focus light on the central region of the retina. In some cases, the optic features are formed in non-optic regions of the ocular lens. In some examples, the optic features have a hexagonal shape, a Fresnel type shape, or a semi sphere shape, but the optic features may have any appropriate shape.

In some instances, the optic features have the same refractive index as the material that makes up the lens body. In other examples, the optic features have a different refractive index than the material of the lens body. The optic features may have the characteristic of directing the light into a peripheral region of the retina, focusing light exactly onto a peripheral region of the retina, focusing light in front of a peripheral region of the retina, focusing light behind a peripheral region of the retina, or combinations thereof. The characteristic may have the effect of controlling growth of an axial length of the eye, controlling myopia, preventing myopia, controlling hyperopia, preventing hyperopia, other effects, or combinations thereof.

The optic feature can be incorporated into the lens body without affecting the ocular lens field of curvature. The optic feature may also be one of multiple independent optic features incorporated into the ocular lens that are independently tuned to direct light towards specific areas of the retina. Such optic features can have different sizes, different shapes, different refractive indexes, different focusing powers, other differing characteristics, or combinations thereof. In some examples, the optic features are lenslets, such as hexagonal lenslets, semi-spherical lenslets, lenslets of another shape, or combinations thereof. In alternative examples, an optic feature include a Fresnel type shape, a toric shape, another type of shape, or combinations thereof.

In another embodiment of the principles described herein, the ocular lens has a body configured to contact an eye. The lens body has an optic zone shaped to direct light towards a central focal point of a central region of the retina. At least one isolated feature of the lens body has a characteristic that directs light into the eye away from the central region of the retina.

The isolated feature can be a molded feature that is integrally formed in the ocular lens. In other instances, the isolated feature is a printed feature. The isolated feature can be formed on an anterior surface of the ocular lens or on an internal surface of a layer of a lens body made of multiple layers.

In yet another embodiment of the principles described herein, a method for making an ocular lens includes forming a spin casting mold with a lens mating surface by forming a profile on a first side of a mold material where the profile contains at least one recess, applying a liquid lens material to the first side of the spin casting mold, spinning the spin casting mold such that the liquid lens material centrifugally flows across the first side of the spin casting mold and fills the recess in the profile, and at least partially curing the liquid lens material to form the ocular lens with at least one protrusion formed by the at least one recess while spinning the spin casting mold.

In yet another embodiment of the principles described herein, a method for making an ocular lens includes forming a spin casting mold with a lens mating surface by forming a profile on a first side of a mold material where the profile contains at least one protrusion, applying a liquid lens material to the first side of the spin casting mold, spinning the spin casting mold such that the liquid lens material centrifugally flows across the first side of the spin casting mold and covers the protrusion in the profile, and at least partially curing the liquid lens material to form the ocular lens with at least one recess formed by the at least one protrusion while spinning the spin casting mold.

In yet another embodiment of the principles described herein, a method for making an ocular lens includes forming a casting mold including a lens mating surface by forming a profile on a first side of a mold material where the profile contains at least one recess, applying a liquid lens material to the first side of the casting mold, securing a backside mold such that the liquid lens material flows across the first side of the casting mold and into the recess in the profile, and at least partially curing the liquid lens material to form the ocular lens with at least one protrusion formed by the at least one recess. In other embodiments, a method includes depositing an optical material onto a supporting surface of an ocular lens where the ocular lens comprises an optic zone shaped to direct light towards a central focal point of a central region of a retina when worn on an eye of a user and the deposited optical material has a characteristic that directs light into the eye away from the central region of the retina.

The Summary is provided to introduce a selection of concepts in a simplified form that are further described below in the Detailed Description. The Summary and the Background are not intended to identify key concepts or essential aspects of the disclosed subject matter, nor should they be used to constrict or limit the scope of the claims. For example, the scope of the claims should not be limited based on whether the recited subject matter includes any or all aspects noted in the Summary and/or addresses any of the issues noted in the Background.

BRIEF DESCRIPTION OF THE DRAWINGS

The accompanying drawings illustrate various embodiments of the principles described herein and are part of the specification. The illustrated embodiments are merely examples and do not limit the scope of the claims.

Throughout the drawings, identical reference numbers designate similar, but not necessarily identical, elements.

DETAILED DESCRIPTION

The growth of the eye's axial length can be affected by visual feedback received in the retina. The visual feedback can be used to balance the axial length of the eye with the collective focusing ability of the cornea and crystalline lens. The eye uses the focal point of the light focused on the retina to determine when the eyes axial length is balanced. Such visual feedback may be based on the entire surface area of the retina, and not just the central portions of the retina dedicated to central vision. Thus, if the periphery of the retina, which has a greater surface area than the central region, receives visual feedback to extend the axial length, the eye may respond by growing to increase the axial length of the eye. This may occur in cases where the central vision is already balanced. Thus, such visual feedback can cause the central vision to become out of focus.

The principles described in the present disclosure include an ocular lens for controlling the light directed towards the peripheral regions of the retina. The principles described herein also include a method and associated components for making such an ocular lens.

The light directed towards the peripheral regions of the retina can provide a stimulus that the eye can interpret as visual feedback to determine a rate of growth for the eye. In some examples, the light directed towards the peripheral regions of the retina is focused exactly on the peripheral regions of the retina. By causing the focal point of the peripherally directed light to be exactly on the retina, the eye may alter the growth rate of the eye so that the axial length of the eye maintains a consistent balance with the eye, focusing power. This may cause the eye to grow slower or stop growing altogether.

In other examples, the light may be focused short of the peripheral regions of the retina. As a result, the focal point of the directed light is in front of the retina. Such a stimulus may cause the eye to have peripheral myopia. This may have the effect of causing the eye to slow growth or stop growing altogether.

Generally, young children begin with a hyperopic condition where the focal point is formed behind the retina. Thus, the eye has an early stimulus to cause the eye to grow in a manner to correct the balance between the eye's focusing power and axial length. In cases where a child has a central hyperopic condition, light can be directed to the peripheral regions of the retina to be purposefully focused behind the retina. This may provide an additional stimulus to the eye to adjust its growth and/or shape which may correct the eye's central vision.

Figure 1:
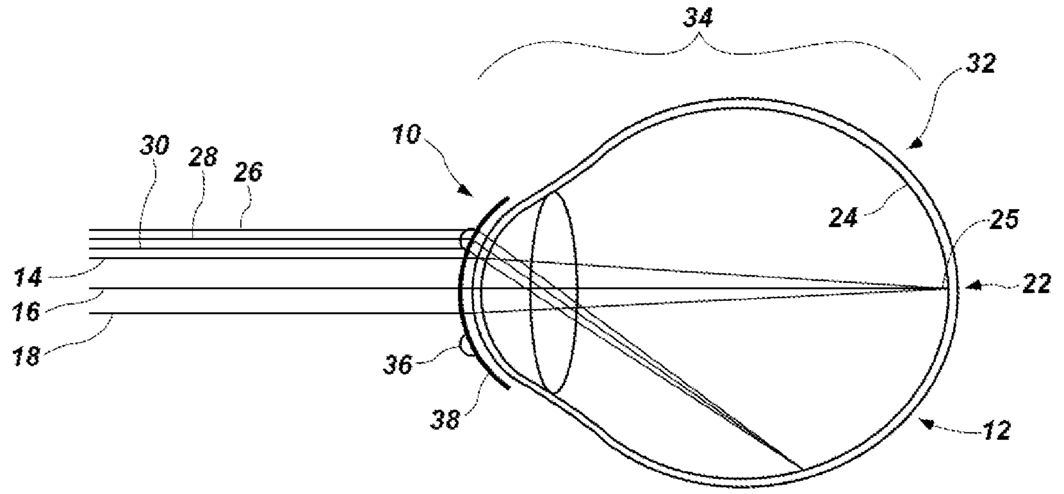
FIG. 1 is cross sectional view of one embodiment of an ocular lens directing light into an eye, according to the principles of the present disclosure.

FIG. 1 is cross sectional view of one embodiment of an ocular lens 10 directing light into an eye 12 according to the principles of the present disclosure. In this example, the ocular lens 10 is placed over the eye 12. Ambient light rays 14, 16, 18 enter the eye 12 after having passed through the ocular lens 10. These rays of light are focused by an optic zone 20 of the ocular lens 10 towards a central region 22 of the retina 24. The focal point 25 of the light rays 14, 16, 18 is formed on the central region 22 of the retina 24, which causes the eye to clearly see objects that are both near and far from the eye.

Other ambient light rays 26, 28, 30 also enter the eye 12 through the ocular lens 10. These light rays 26, 28, 30 are refracted differently than light rays 14, 16, 18. Light rays 26, 28, 30 are directed towards the peripheral region 32 of the retina 24. In the example of FIG. 1, the light rays 26, 28, 30 are focused on the peripheral region 32 of the retina 24. This may cause the eye 12 to have a stimulus that indicates that the focusing power of the eye and the axial length 34 are balanced. Thus, the eye 12 may be induced to maintain its current ratio between the focusing power and axial length 34.

Light rays 26, 28, 30 are refracted differently than light rays 14, 16, 18 because light rays 26, 28, 30 pass through the ocular lens 10 at an exemplary feature 36 that has a different refractive property than the refractive properties in the optic zone 20 of the ocular lens 10. According to one exemplary embodiment, the feature 36 may be a feature made of a material with a different refractive index than the material making up the optic zone 20 of the ocular lens 10. The feature may include a material that is a silicone material, a hydrogel material, tefilcon, tetrafilcon A, crofilcon, helfilcon A&B, mafilcon, polymacon, hioxifilcon B, lotrafilcon A, lotrafikon B, galyfilcon A, senofilcon A, sifilcon A, comfilcon A, enfilcon A, lidofilcon B, surfilcon A, lidofilcon A, alfafilcon A, omafilcon A, vasurfilcon A, hioxifilcon A, hioxifilcon D, nelfilcon A, hilafilcon A, acofilcon A, bufilcon A, deltafilcon A, phemfilcon A, bufilcon A, perfilcon, ctafilcon A, focofilcon A, ocufilcon B, ocufilcon C, ocufilcon D ocufilcon E, ocufilcon F, phemfilcon A, methafilcon A, methafilcon B, vilfilcon A, other types of polymers, or combinations thereof. These materials may include various combinations of monomers, polymers, and other materials to form the final polymer. For example, common components of these materials may include HEMA, HEMA-GMA, and the like.

In some embodiments, the ocular lens 10 has a thickness of approximately 0.01 mm to approximately 0.14 mm. The thickness of the ocular lens 10 can vary at different locations on the ocular lens 10. For example, the ocular lens 10 can be thicker near the outer edge of the ocular lens 10 than in the optic zone 20. In some examples, the feature 36 may be an additive feature that adds to the thickness of the ocular lens 10. In other examples, the feature 36 is a subtractive feature that reduces the thickness of the lens. In yet other examples, the feature 36 replaces the material that otherwise makes up the ocular lens 10. For example, sections of the ocular lens may be replaced with the material that makes up the features 36.

The feature 36 may be formed in any number of ways including, but in no way limited to, designing the feature into a cast mold configured to form a cast molded contact lens or a spin-cast mold that is used to form a spin-cast soft contact lens, forming the feature in an intermediate layer of a composite-type lens, adding material on the exterior surface 38 of the ocular lens 10 via deposition via a printing process or a multi-stage curing process, and the like. In the exemplary embodiment that includes printing the feature 36, such printing processes may include pad printing processes, plate printing processes, etch printing processes, dot matrix printing processes, laser printing processes, tamp printing processes, liquid jet printing processes, other types of processes, or combinations thereof. In other examples, the feature is added to a surface of the ocular lens through another mechanism, such as spraying techniques, vapor deposition techniques, droplet techniques, coating techniques, other types of techniques, or combinations thereof.

According to one exemplary embodiment, the features 36 configured to direct light into the peripheral regions of the retina may be integrally formed in the ocular lens 10. In such examples, the features 36 are made of the same material as the material that makes up the rest of the ocular lens 10. According to this embodiment, the refractive index of the features 36 is the same as the refractive index of the material of the ocular lens 10. However, a geometry of the features 36, an increased thickness of the features 36, a refractive property of the features 36, or another property of the features 36 may result in causing the light rays 26, 28, 30 to be selectively directed towards the peripheral region 32 of the retina 24.

In some examples, the ocular lens 10 is a contact lens, a soft contact lens, a rigid gas permeable contact lens, an implantable contact lens, another type of lens, or combinations thereof. In the example of FIG. 1, the optic zone 20 is free of the features 36. As a result, there is little to no effect from the feature to the eye's central vision. However, multiple, independent features 36 divert some of the light contacting the ocular lens 10 in non-optic regions that would not otherwise enter the eye, or would enter the eye in a different manner. Thus, an increased amount of light enters the eye 12 due to the off-axis positioning of the optic features 36. At least most of the light rays that would otherwise enter the eye and travel towards the peripheral region 32 of the eye 12 without the features 36 continue to enter the eye 12 without aid of the features 36. This light already provides visual feedback to the eye that affects eye growth. However, the additional light redirected by the features 36 into the eye can be controlled to counteract that visual feedback, to enhance that visual feedback, to modify that visual feedback, or otherwise provide a stimulus that affects to eye growth. The additional visual feedback can be used to control myopia progression or, in some cases, prevent myopia from occurring. The amount of light directed towards the peripheral region 32 of the retina 24 may be selected based on the amount of light needed to obtain the desired effect on the eye growth. In some cases, minor amounts of additional light directed from the features 36 are sufficient to achieve the desired results. However, in other cases, directing more light may be beneficial to overcome a strong natural stimulus that causes undesirable axial length growth.

Figure 2:
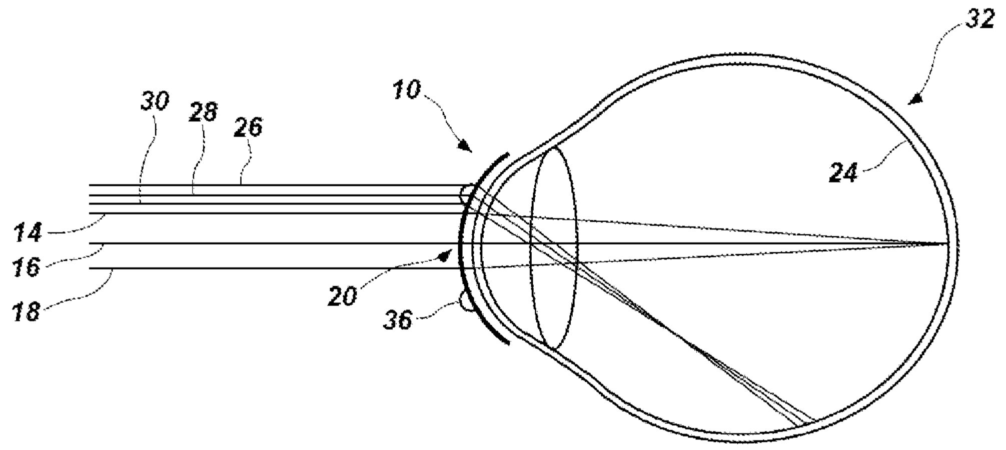
FIG. 2 is cross sectional view of one embodiment of an ocular lens directing light into an eye, according to the principles of the present disclosure.

FIG. 2 is cross sectional view of one embodiment of an ocular lens 10 directing light into an eye 12 according to the principles of the present disclosure. In this example, the features 36 direct the light towards the peripheral region 32 of the retina, but the focal point 25 of the directed light is formed in front of the retina 24. Thus, the light rays 26, 28, 30 directed by the features 36 cause a peripheral myopic condition. Such a stimulus may indicate stopping or slowing the growth of the axial growth of the eye 12. In some examples, such a peripheral myopic stimulus may provide a stronger stimulus to the eye 12 to change the eye's growth, without adversely affecting the user's vision since the light in the optic zone is correctly focused on the retina. In some example, directing the redirected light rays 26, 28, 30 to focus short of the peripheral region 32 of the retina 24 may be desirable to treat cases of myopia because such a stimulus indicates that the axial length 34 is too long.

Figure 3:
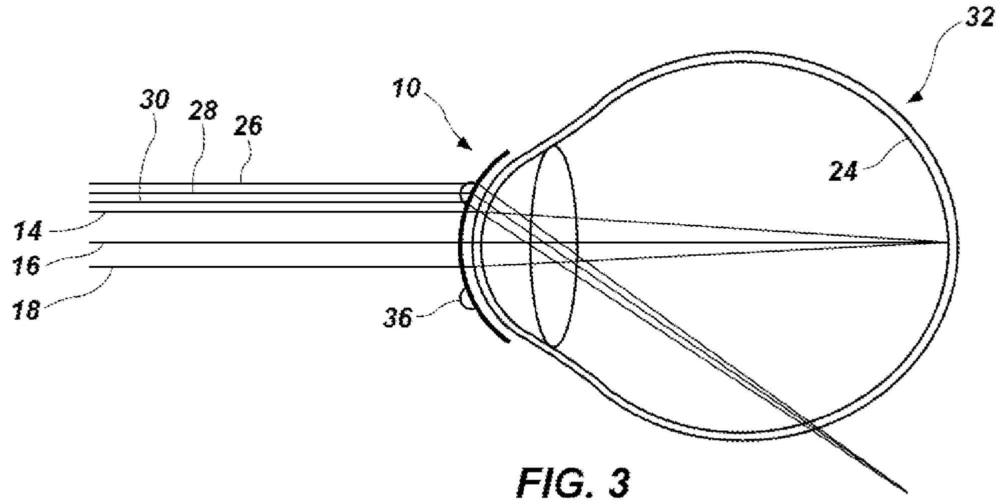
FIG. 3 is cross sectional view of one embodiment of an ocular lens directing light into an eye, according to the principles of the present disclosure.

FIG. 3 is cross sectional view of one embodiment of an ocular lens 10 directing light into an eye 12 according to the principles of the present disclosure. In this example, the features 36 direct the light towards the peripheral region 32 of the retina, but the focal point 25 of the directed light is formed behind the retina 24. Thus, the light rays 26, 28, 30 directed by the features 36 cause a peripheral hyperopic condition. Such a stimulus may indicate to increase the axial growth of the eye 12. In some examples, such a peripheral hyperopic stimulus may provide a stimulus to the eye 12 to change the eye's growth rate. In some examples, directing the redirected light rays 26, 28, 30 to focus behind of the peripheral region 32 of the retina 24 may be desirable to treat cases of hyperopia because such a stimulus may signal that the axial length 34 is too short. Similar to the embodiment illustrated in FIG. 2, the desired stimulus of FIG. 3 is provided outside the optic zone and the users immediate optical experience is not adversely affected.

While FIGS. 1-3 have been described with reference to focusing the redirected light within a three dimensional space with reference to the retina 24, the feature 36 may direct light into the peripheral space of the vitreous chamber 40 of the eye 12 for any appropriate reason. For example, the light may be directed into the peripheral space without a predetermined focus. In other examples, the light may be directed into the peripheral space with a predetermined focus as described in FIGS. 1-3. In some cases, the light may be directed into the peripheral space of the vitreous chamber 40 for treating conditions other than myopia and hyperopia. For example, the light may be directed into the peripheral space for treating other conditions, for entertainment purposes, for communicating with a device implanted in the eye, for other purposes, or combinations thereof.

Further, FIGS. 1-3 are depicted with a limited number of features directing light to limited areas of the retina for illustrated purposes. Multiple, independent features can focus light to multiple areas of the retina. Each of the independent features can be customized to specific circumstances of the eye. For example, some of the features may include varying degrees of focusing power, refractive properties, shapes, sizes, materials, thicknesses, other physical characteristics, other chemical characteristics, other characteristics, or combinations thereof. Different optic features of the same ocular lens may independently focus light in front of, on, or behind the retina. In other examples, different areas of the retina receive different intensities of redirected light.

In some examples, the features are constructed so that the wavelengths of the redirected light are not separated. In other words, the features may direct the all wavelengths within the visual light spectrum together. However, in some examples, at least some of the features may be constructed to redirect just selected wavelengths of light towards to the peripheral areas of the retina.

FIGS. 4A-9 illustrate various components that can be used in certain examples for making an ocular lens 10 having the features 36. While the present exemplary systems and methods are described below primarily in the context of a spin cast contact lens formed in an injection molded spin cast mold 42, the present systems and methods may also be equally applied to lenses manufactured from spin casting, cast molding, and/or turning.

Figure 4A:
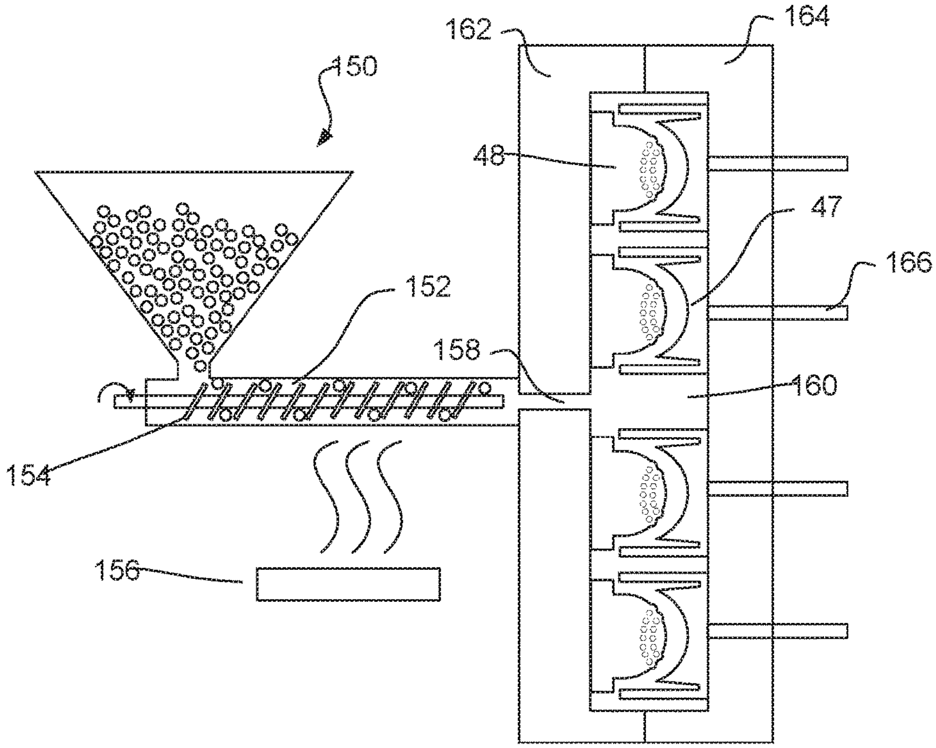
FIG. 4A is a cross sectional view of one embodiment of an injection molding machine configured to form a spin casting mold to make an ocular lens, according to the principles of the present disclosure.

With reference to spin cast contact lenses, the features present on the anterior surface of the lens are typically designed into the mold used in the manufacture of the lens. FIG. 4A is a cross sectional view of one embodiment of making molds 42 for the production of ocular lenses 10 according to the principles of the present disclosure. In this example, an injection molding process is used to form the mold 42. As shown, a standard injection molding machine may be used to form the molds 42. Specifically, material for the molds is fed through a funnel 150 to a cylinder 152. The cylinder 152 may include a screw 154 or another type of mechanism that is configured to move the molding material along the length of the cylinder 152. Additionally, a heating mechanism 156 is applied to the cylinder to melt or at least soften the molding material as the molding material is passed through the cylinder 152. At a nozzle 158 of the cylinder 152, the molding material is extruded into a cavity 160 collectively formed by a first part 162 and a second part 164.

Figure 4B:
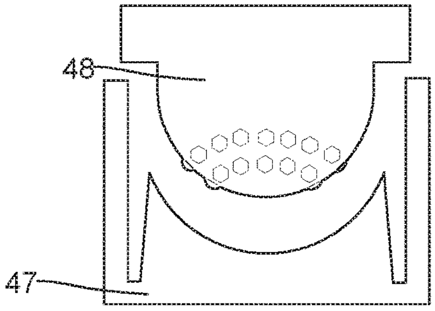
FIG. 4B is a cross sectional view of one embodiment of forming a spin casting mold to make an ocular lens, according to the principles of the present disclosure.
Figure 5:
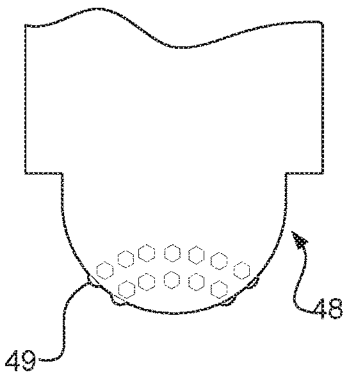
FIG. 5 is a cross sectional view of one embodiment of an mold used for making a spin casting mold for an ocular lens, according to the principles of the present disclosure.

As illustrated in FIGS. 4A and 4B, the cavity 160 includes male mold tooling 48 and female mold tooling 47 that are respectively aligned with one another. The extrusion pressure of the molding material entering the cavity 160 causes the molding material to fill all of the void space within the cavity 160 including the space between the male mold tooling 48 and female mold tooling 47. The geometry of the male mold tooling 48 and female mold tooling 47 is transferred to the resulting spin cast molds 42 for spin casting the ocular lens 10. As illustrated in FIGS. 4B and 5, male mold tooling 48 of the spin casting mold 42 may include protrusions 49 that resemble the desired shape and size of the features 36.

To generate features 36 having the desired optical properties, the male mold tooling 48 is precisely machined to match the features desired on the final ocular lens to be produced according to the present exemplary system and methods. Any number of precise machining and forming methodologies may be used to form the male mold tooling including, but in no way limited to, DAC ophthalmic lathes, Optoform ophthalmic lathes, FTS tooling, 5-axis diamond milling, 3-dimensional nano-printing, nanolithography, fused deposition, and the like. After the molding material has had a sufficient time to harden within the cavity 160, the first part 162 and the second part 164 are separated, and the molds are removed via ejector pins 166.

A liquid lens material 52 can be applied to a profile 54 of the spin casting mold 42 formed by the male mold tooling 48. The spin casting mold 42 with the liquid lens material 52 can be loaded into a spinning structure 68 or spin tube that is configured to spin the spin casting mold 42 so that the liquid lens material 52 centrifugally spreads across to the profile 54 into the desired shape of the ocular lens, which includes filling the recesses 55 of the profile 54. A curing agent (i.e., temperature, actinic radiation, or another type of curing agent) is exposed to the liquid lens material 52 while the spin casting mold 42 is spinning. As a result, the liquid lens material 52 forms the ocular lens 10 with the features 36 formed on the ocular lens' anterior surface 38.

Figure 6:
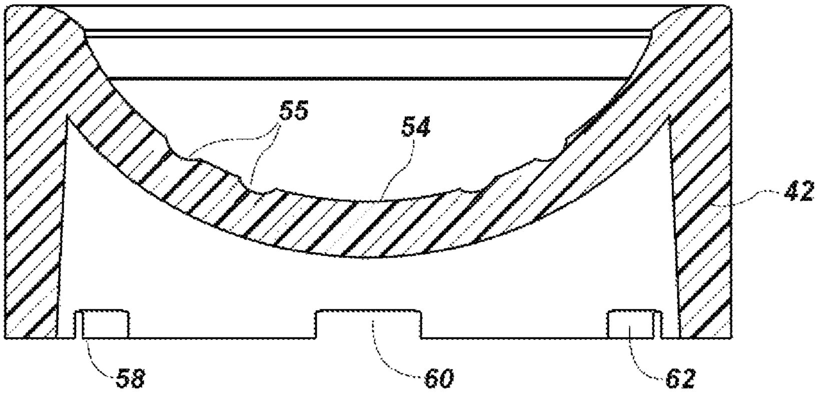
FIG. 6 is a cross sectional view of one embodiment of a spin casting mold for an ocular lens, according to the principles of the present disclosure.

FIG. 6. is a cross sectional view of one embodiment of a spin casting mold for an ocular lens according to the principles of the present disclosure. In this example, the spin casting mold 42 has a base 56 with multiple cut outs 58, 60, 62 that are configured to allow the passage of an inert gas between the molds during the spinning and curing process. The profile 54 of the spin casting mold 42 is shaped to form the anterior surface of the ocular lens 10. The recesses 55 formed in the profile 54 correspond to the protrusions formed in the male mold tooling 46.

Figure 7:
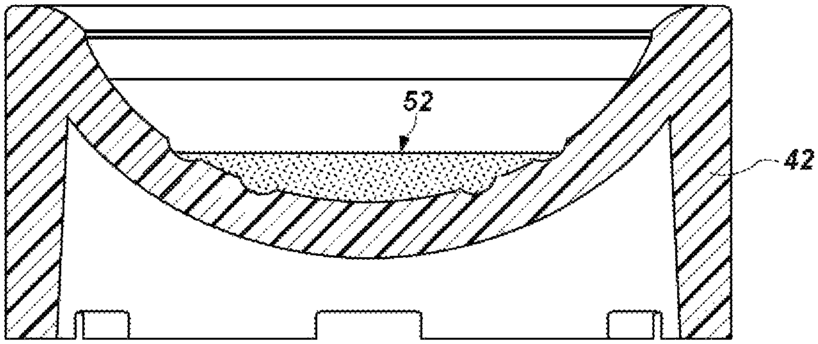
FIG. 7 is a cross sectional view of one embodiment of a spin casting mold with a liquid lens material, according to the principles of the present disclosure.

FIG. 7 is a cross sectional view of one embodiment of a spin casting mold 42 with a liquid lens material 52 according to the principles of the present disclosure. In this example, the liquid lens material 52 is deposited into the profile 54 of the spin casting mold.

The liquid lens material 52 can be made from any material suitable for use in contact lenses. For example, the liquid lens material 52 can be made of any silicone material and/or hydrogel material. Such material may be formed of polymers, such as tefilcon, tetrafilcon A, crofilcon, helfilcon A&B, mafilcon, polymacon, hioxifilcon B, lotrafilcon A, lotrafilcon B, galyfilcon A, senofilcon A, sifilcon A, comfilcon A, enfilcon A, lidofilcon B, surfilcon A, lidofilcon A, alfafilcon A, omafilcon A, vasurfilcon A, hioxifilcon A, hioxifilcon D, nelfilcon A, hilafilcon A, acofilcon A, bufilcon A, deltafilcon A, phemfilcon A, bufilcon A, perfilcon, ctafilcon A, focofilcon A, ocufilcon B, ocufilcon C, ocufilcon D ocufilcon E, ocufilcon F, phemfilcon A, methafilcon A, methafilcon B, vilfilcon A, other types of polymers, monomers, or combinations thereof. These materials may include various combinations of monomers, polymers, and other materials to form the liquid lens material.

In one embodiment, the liquid lens material is made of hydrogel polymers without any silicone. This may be desirable to increase the wettability of the ocular contact lens. In another embodiment, the liquid lens material is made of silicone hydrogel material.

The ocular lens 10 can be shaped and sized based on a variety of factors, including the shape and size of the users eye and various optical properties to be achieved by the optic zone of the ocular lens. The total thickness of the ocular lens 10 can be approximately 0.1 mm to approximately 0.14 mm. The thickness of the ocular lens 10 can gradually vary at different locations on the ocular lens 10. For example, the ocular lens 10 can be thicker near the outer edge of the ocular lens 10 than in the optic zone. However, the features 36 may cause the cross sectional thickness of the ocular lens 10 to vary sharply in isolated locations across the anterior surface 38 of the ocular lens 10.

Figure 8:
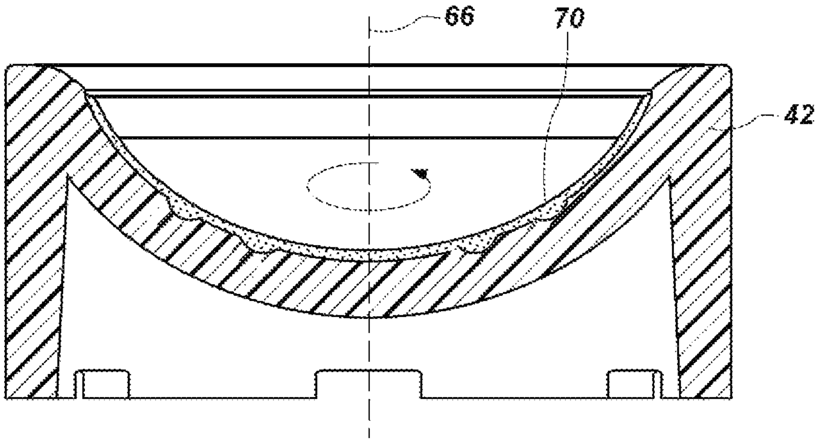
FIG. 8 is a cross sectional view of one embodiment of a spin casting mold with a liquid lens material centrifugally spreading across a profile of the spin casting mold, according to the principles of the present disclosure.

FIG. 8 is a cross sectional view of one embodiment of a spin casting mold 42 with a liquid lens material 52 centrifugally spreading across a profile 54 of the spin casting mold 42 according to the principles of the present disclosure. In this example, the spin casting mold 42 is spun around a central axis 66 within a spinning structure (68, FIG. 9) or spin tube. The spinning structure 68 is rotated at a speed and in such a way that forms the desired posterior surface 70 of the ocular lens 10.

Figure 9:
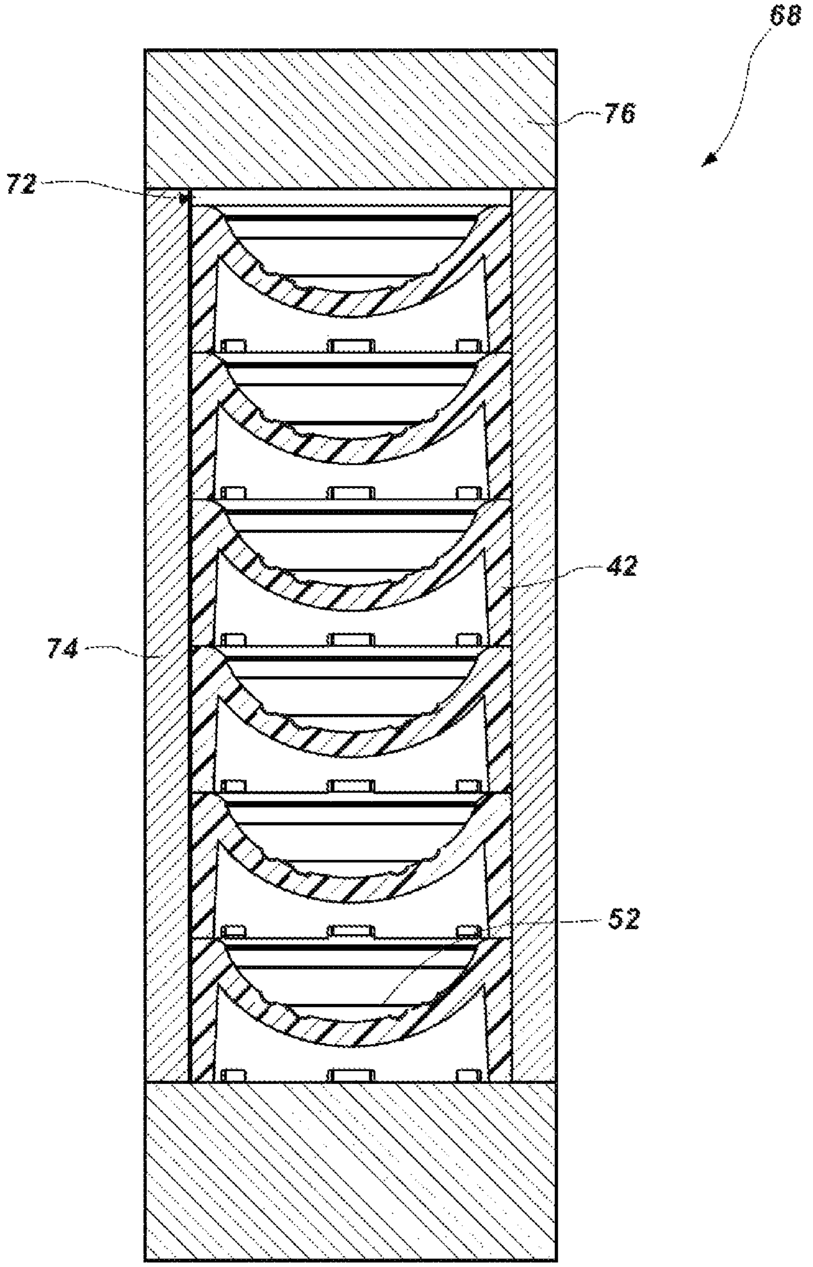
FIG. 9 is a cross sectional view of one embodiment of a spinning structure used to shape and cure spin casting molds for making ocular lenses, according to the principles of the present disclosure.

The spinning structure 68 illustrated in FIG. 9 includes a central loading region 72 that is configured to receive the spin casting molds 42 that contain the liquid lens material 52. The central loading region 72 may be formed by a glass tube, a metal tube, or another type of structure that can retain the spin casting molds 42 in a stacked orientation. In examples where actinic radiation is used as the curing agent, the spinning structure 68 is an opaque material that includes sufficient openings to allow the actinic radiation into the central loading region 72. In the example of FIG. 9, the spinning structure 68 includes a glass sidewall 74 that retains the spin casting molds 42 in a stacked orientation. The spinning structure 68 also includes a region 76 that can be used to attach to a spinning driver, such as a motor.

The spinning structure 68 is programmed to rotate in a precise manner to form the desired posterior surface 70 of the ocular lens 10, which is the surface of the ocular lens that is intended to contact the eye. The program that causes the spinning structure 68 to rotate can be modified to create a desired profile for individual prescriptions. The curing agent is applied to the liquid lens material 52 while the spinning structure 68 rotates the spin casting molds 42. As a result, the ocular lens 10 is formed while the spinning structure rotates. In some examples, the ocular lenses are fully cured within the spinning structure. However, in other examples, ocular lens 10 may be fully cured over the course of multiple curing stages. For example, the ocular lens may be cured in the spinning structure 68 to a point where the liquid lens material 52 retains its shape but is not fully cured. At this stage, the spin casting mold with the ocular lens may be removed from the spinning structure to finish curing in an environment that is more cost effective. A spinning structure that is compatible with the principles described herein is described in U.S. Patent Publication 2012/0133064 issued to Stephen D. Newman. U.S. Patent Publication 2012/0133064 is herein incorporated by reference for all that is discloses.

Figure 10:
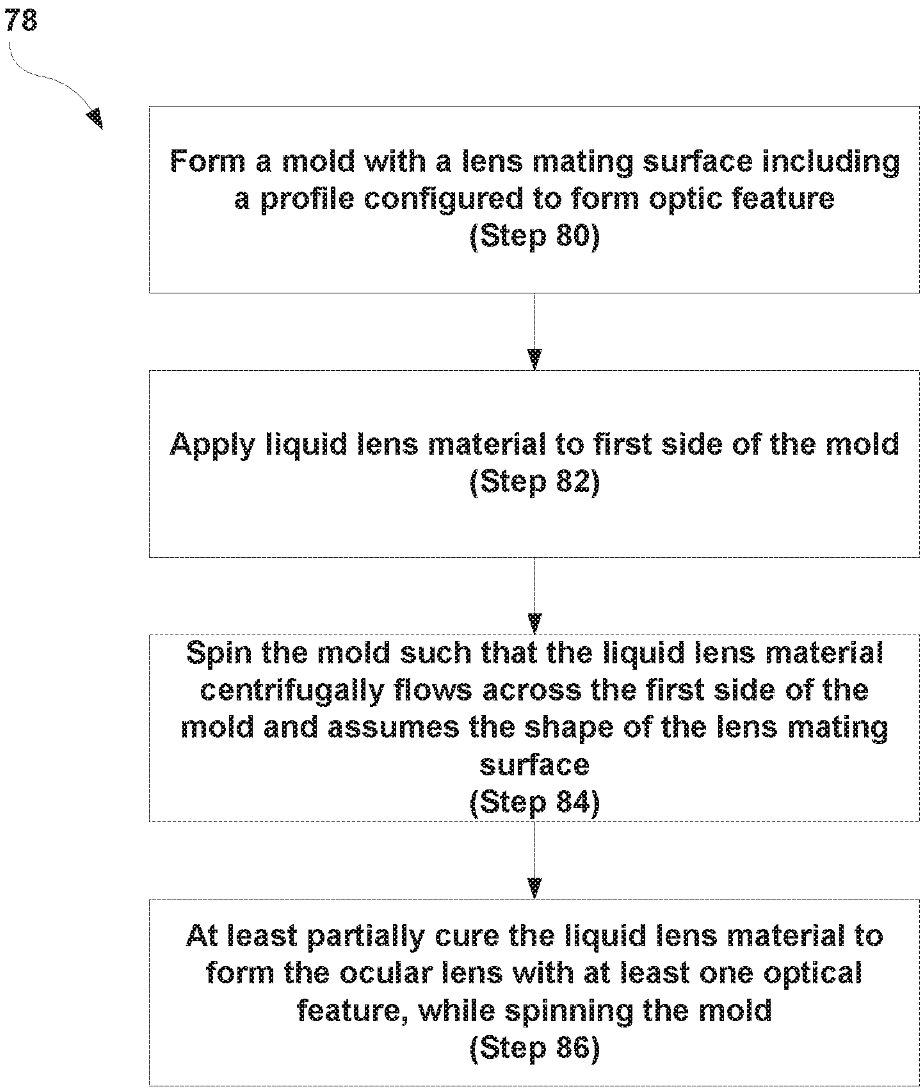
FIG. 10 is a block diagram of one embodiment of a method for making ocular lenses, according to the principles of the present disclosure.

FIG. 10 is a block diagram of one embodiment of a method 78 for making ocular lenses according to the principles of the present disclosure. In this example, the method 78 includes forming a mold with a lens mating surface by forming a profile in a first side of the mold material where the profile contains at least one negative of an optic feature (step 80). According to one exemplary embodiment, the profile may be injection molded using a male mold tooling 48 as described in reference to FIGS. 4A-5. The method may also include applying the lens material to the first side of the mold (step 82) and spinning the mold such that the liquid lens material centrifugally flows across the first side of the spin casting mold and fills the at least one negative of an optic feature formed on the profile (step 84). The liquid lens material is then at least partially cured to form the ocular lens with at least one protrusion formed by the at least one recess while spinning in the spin casting mold (step 86). The optic feature may be any feature that redirects light into the peripheral space of the vitreous chamber of the eye towards the peripheral retina when worn on an eye.

While the examples described above with reference to FIGS. 4A-10 have been described with specific reference to forming a protrusion on the anterior surface of the ocular lens to create the feature, any appropriate mechanism for forming the ocular lens and its associated features may be used in accordance with the principles described in the present disclosure. For example, a different material may be applied to the spin casting mold and cured within just the recesses to form the protrusions prior to applying liquid lens material. In such an example, the protrusions are formed with a different material than the rest of the lens body. During a later curing process, such protrusions may be bonded to the rest of the lens body. Further, the protrusions may be formed outside of a spinning process and bonded to the body of the ocular lens through a curing process, a bonding process, or through any other type of appropriate process for adding an optical feature on a contact lens.

Figure 11:
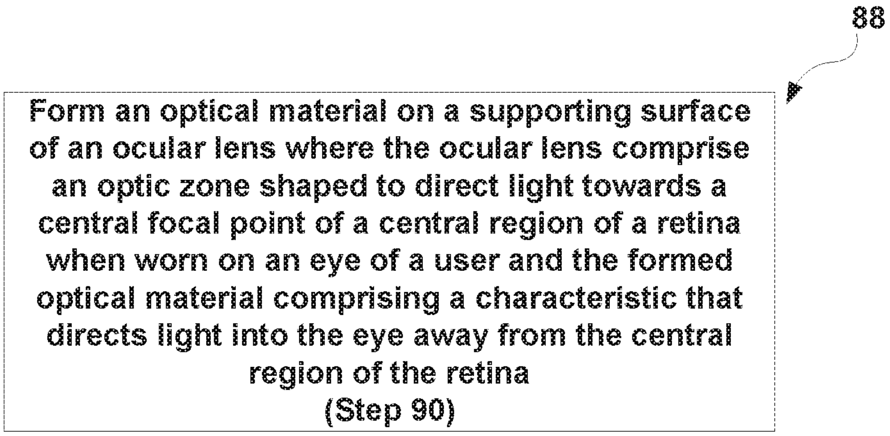
FIG. 11 is a block diagram of one embodiment of a method for making ocular lenses, according to the principles of the present disclosure.

In yet other examples, the features are deposited on the lens hotly. Such an example is described in FIG. 11. In this example, the method 88 includes depositing 90 an optical material on a supporting surface of an ocular lens where the ocular lens comprises an optic zone shaped to direct light towards a central focal point of a central region of a retina when worn on an eye of a user and the deposited optical material comprises a characteristic that selectively directs peripheral light into the eye away from the central region of the retina when worn on an eye.

In such an example, the optical material may be made of the same material as the lens body, or the optical material may be made of a different type of material with a different index of refraction. In either case, the features may be formed such that they direct light towards the peripheral regions of the retina. The features can be deposited on the anterior, posterior, or intermediate surface of the lens body through the use of printing techniques. Such printing techniques may include, but are not limited to, pad printing, plate printing, etch printing, dot matrix printing, dye sublimation and carrier sheet (laser printing), use of photosensitive elements that receive subsequent laser treatment, other types of printing techniques, or combinations thereof.

In one embodiment, the printing method is a tamp printing technique. Tamp printing techniques include one method of pad printing that uses a laser etched pad to transfer the material to form the features to the ocular lens. The pad tamps a reservoir of such material each time before the pad tamps the ocular lens. Machines capable of printing in this fashion are available from TAMPOPRINT AG, which is headquartered in Korntal-Münchingen, Germany.

In another embodiment, such material can be printed on the ocular lens using an liquid jet printing system. In one embodiment, the material has a liquid characteristic that is capable of being injected from a pressure inkjet cartridge, a thermal inkjet cartridge, another type of ink cartridge, or combinations thereof. Such a liquid may include a silicone material.

Figure 12:
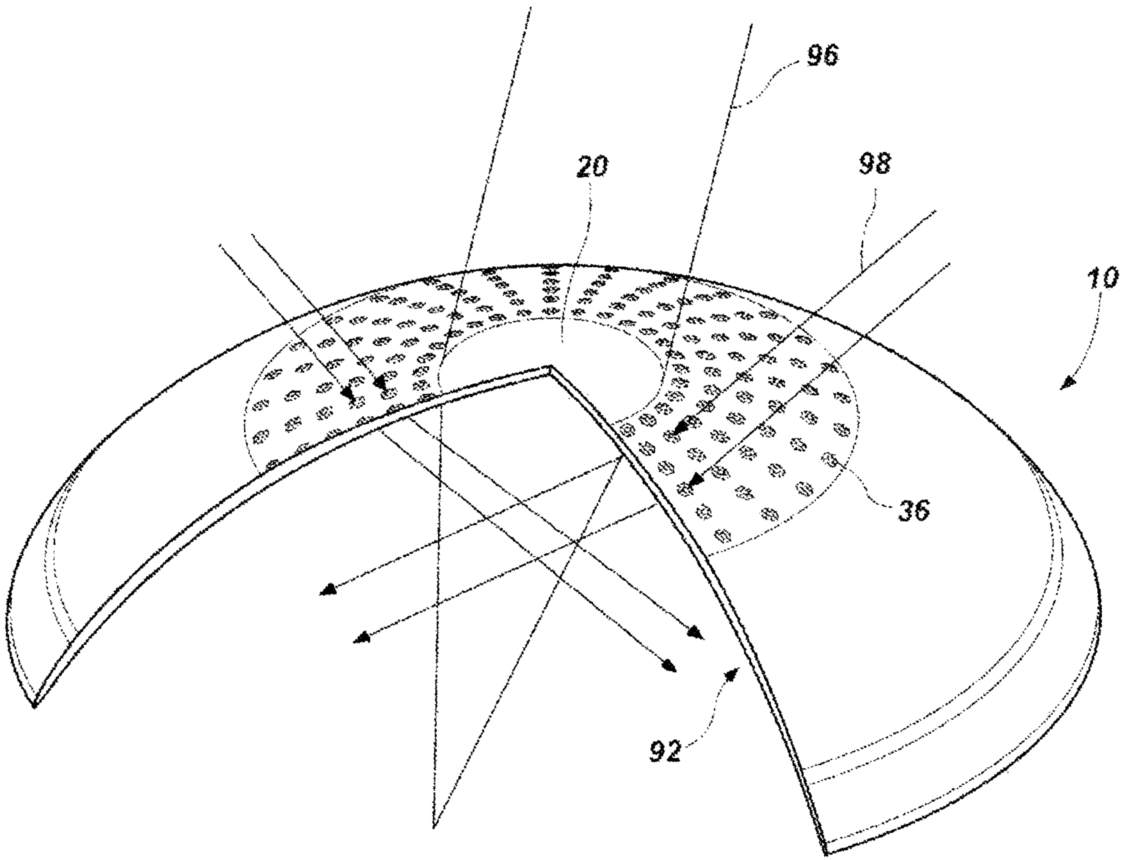
FIG. 12 is a partial cross-sectional perspective view of one embodiment of an ocular lens with features for directing the light off axis towards a peripheral region of the retina, according to the principles of the present disclosure.
Figure 13:
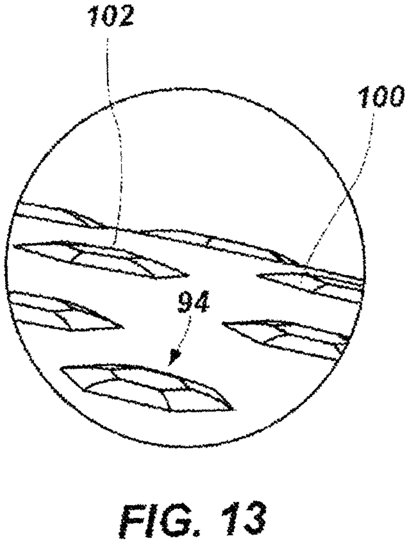
FIG. 13 is a magnified view of one embodiment of a feature for directing light towards a periphery of a retina, according to the principles of the present disclosure.
Figure 14:
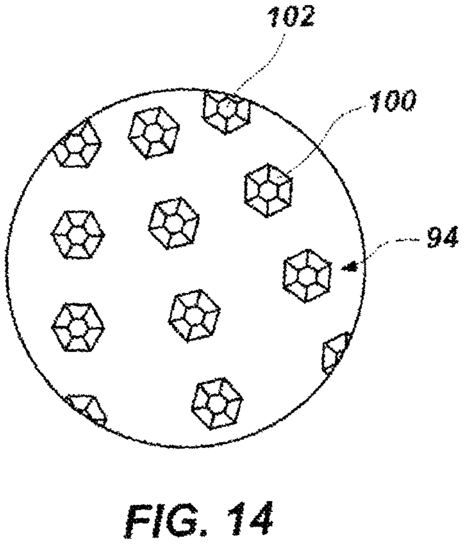
FIG. 14 is a magnified view of one embodiment of a feature for directing light towards a periphery of a retina, according to the principles of the present disclosure.

FIG. 12 is a perspective view of one embodiment of an ocular lens 10 with features 36 for directing the light off axis towards a peripheral region of the retina according to the principles of the present disclosure. In this example, the ocular lens 10 includes an optic zone 20 and a non-optic region 92. The features 36 are formed in the non-optic region 92. FIGS. 13-14 depict features 36 formed with hexagonal shapes 94.

As illustrated in FIG. 12, the optic zone 20 is configured to focus central light 96 passing through the optic zone on the retina 24 in the central region 22 of an eye on which the ocular lens 10 is worn. The optic zone 20 is positioned in front of the eye's pupil. Often, the non-optic region 92 circumscribes the optic zone 20 and makes up the remainder of the ocular lens 10. This non-optic region 92 may be positioned over the iris and, in some cases, portions of the conjunctiva and sclera of the eye. Traditionally, light passing through the non-optic region 92 of the ocular lens 10 does not enter the eye because such light rays would make contact with regions of the eye that do not permit light to enter, such as the iris and sclera. However, in contrast to traditional lenses, the features 36 incorporated into the ocular lens 10 direct peripheral light rays 98 (that would not otherwise be on a trajectory to enter the eye) into the pupil at an angle that, by design, directs the peripheral light towards the peripheral region 32 of the retina 24.

The peripheral light 98 redirected into the eye may not affect the central vision of the eye because the peripheral light 98 is directed into the peripheral region 32 of the retina where peripheral vision is processed. Consequently, the peripheral light 98 that is directed towards the peripheral region 32 of the retina 24 can be intentionally defocused to provide a desired stimulus to the eye. For example, the redirected peripheral light 98 may be focused exactly on the retina. In some cases, such a stimulus may indicate that the eye's axial length is properly proportioned with the eye's focusing power. In other examples, the redirected light rays 98 are focused to fall short of the retina. In some cases, such a stimulus indicates that the eye's axial length is too long for the eye's focusing power, thereby slowing or ceasing the axial growth of the eye. In yet other cases, the redirected light rays 98 can be focused behind the retina, which may create a stimulus that indicates the eye's axial length is too short for the eye's focusing power. Depending on the eye's ability to grow, the eye may be caused to grow in such a manner to at least partial improve the balance between the axial length of the eye and the eye's focusing power based on the stimulus.

The amount of light that is redirected to the peripheral region 32 of the retina 24 is hazed on the number of features 36, the refractive index of the features 36, the shape of the features 36, other factors, and combinations thereof. An ocular lens 10 may be customized for conditions of the eye. For example, in cases where a professional feels that a strong stimulus is desirable, more features 36 may be added to the ocular lens to redirect more light or the focusing power of selected features may be increased. In other examples, a material with certain refractive indexes or features with different shapes may be used to achieve the desired strength of the stimulus. Likewise, these parameters may be scaled down to reduce the strength of the stimulus as desired based on a different eye's condition.

The hexagonal shape 94 of the features is further illustrated in FIGS. 13 and 14. As shown, according to one exemplary embodiment, the hexagonal shape 94 may include six contiguous side faces 100 that border a central face 102. The side faces 100 may be angled precisely to direct the light rays to the desired portion of the vitreous chamber of the eye. The height of the hexagonal shape 94 may be dependent on the desired angle of the side faces 100. Further, the angle of the side faces 100 may also determine the width, length, and other dimensions of the feature 36. The density and spacing of the features may also be determined by the desired intensity of the stimulus. The junctions between the side faces 100 and the junctions between the side faces 100 and the central 102 may be rounded, beveled, sharp, or otherwise contoured to provide desirable optical properties or for convenience in manufacturing.

Figure 15:
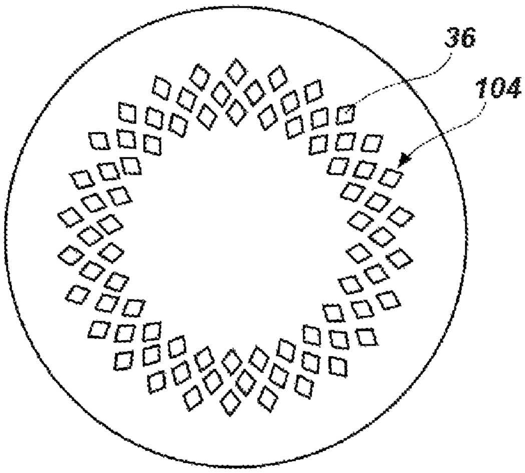
FIGS. 15-18 are front views of exemplary embodiments of ocular lenses, according to the principles of the present disclosure.
Figure 16:
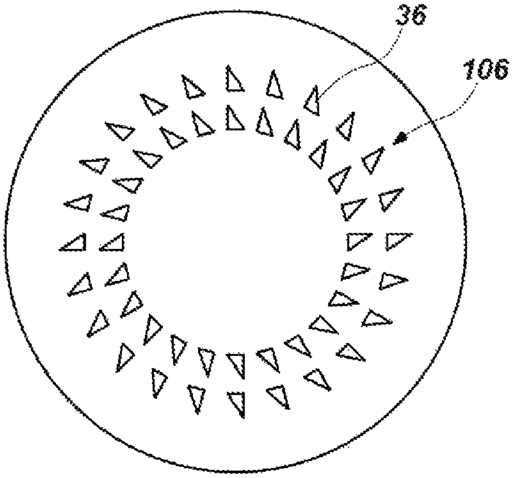
Figure 17:
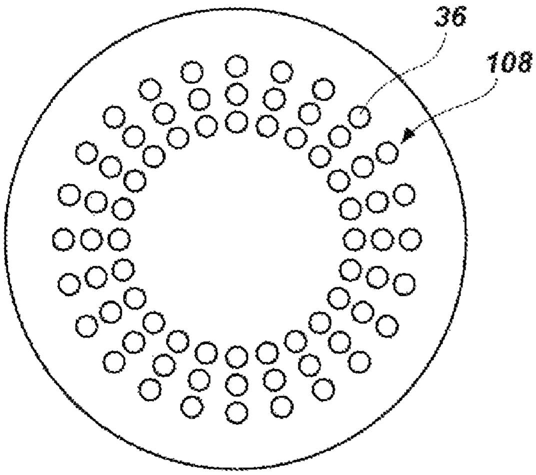
Figure 18:
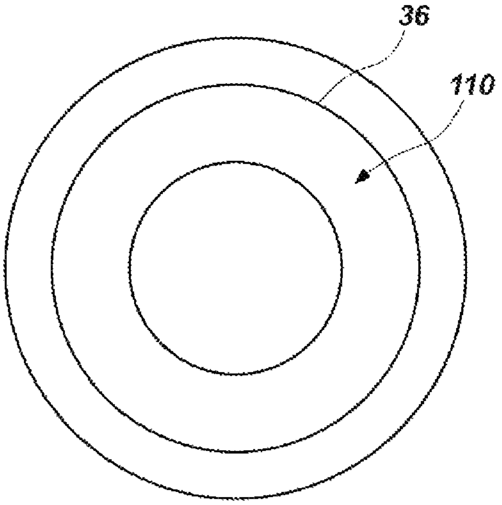

While this example has been described with reference to features 36 with hexagonal shapes 94, any appropriate type of shape may be used in accordance with the principles described herein. For example, FIGS. 15-18 depict other arrangements of features with different shapes that may be used to redirect light toward the peripheral region 32 of the retina 24. In the example of FIG. 15, the features include diamond shapes 104. In the example of FIG. 16, the features include triangular shapes 106. In the example of FIG. 17, the features include circular shapes 108. FIG. 18 depicts a single feature 36 that encompasses a majority of the non-optic zone 110. In this example, the shape may be a ring deposited or otherwise formed on the anterior surface 38 of the ocular lens or in an intermediate layer of the lens. In such examples, the material used to make the feature 36 with the solid shape 110 may include a dye, pigment, another type of coloring agent that may cause an eye that wears such an ocular lens 10 to appear to have an eye color of the feature 36. Such an ocular lens 10 may be worn by those who desire to change their eye color.

Figure 19:
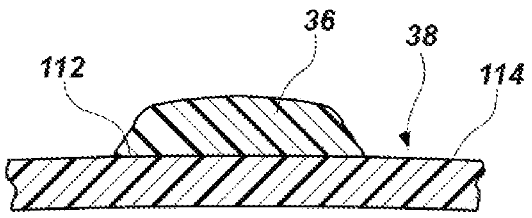
FIGS. 19-21 are cross sectional views of exemplary embodiments of the features of the ocular lens, according to the principles of the present disclosure.
Figure 20:
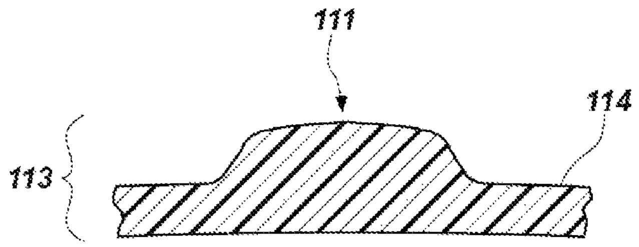
Figure 21:
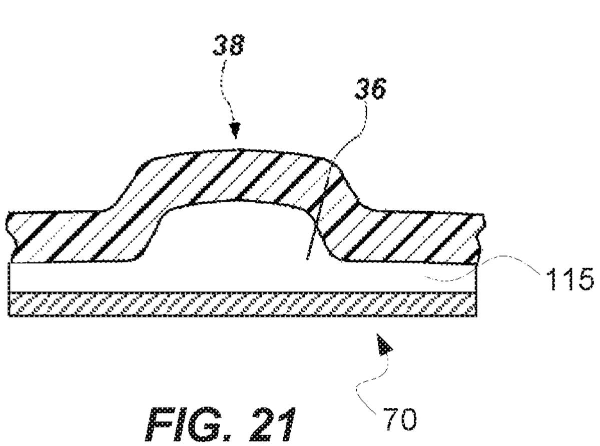

FIGS. 19-21 depict various cross sectional views of the features 36 according to the principles described in the present disclosure. For example, FIG. 19 discloses a feature 36 that is deposited on the anterior surface 38 of the ocular lens. In this example, there is an interface 112 between the deposited material of the feature 36 and the lens body 114. The deposited material may have a characteristic that causes it to adhere to the lens body 114. Such a characteristic may include an electrostatic attraction, an adhesive component, cross-linking of the polymers, another type of characteristic, or combinations thereof. Such a feature may be made with the processes that were described in conjunction with FIG. 11.

FIG. 20 depicts a feature 36 that is integrally formed with the lens body 114. Such a feature may be made with the processes that were described in conjunction with FIGS. 4A 10. In such an example, the cross-sectional thickness 113 of the ocular lens 10 increases in an isolated location 111 of the ocular lens. FIG. 21 depicts a feature 36 that includes an isolated change in the gradual curve of the anterior surface 38 due to an intermediate layer formed in a composite lens. As illustrated in FIG. 21, a composite lens is illustrated including an anterior surface 38, an intermediate layer 115 including a feature 36, and a posterior layer forming the posterior surface 70. Further details of a composite lens including multiple layers will be provided below with reference to FIGS. 22 31.

Figure 22:
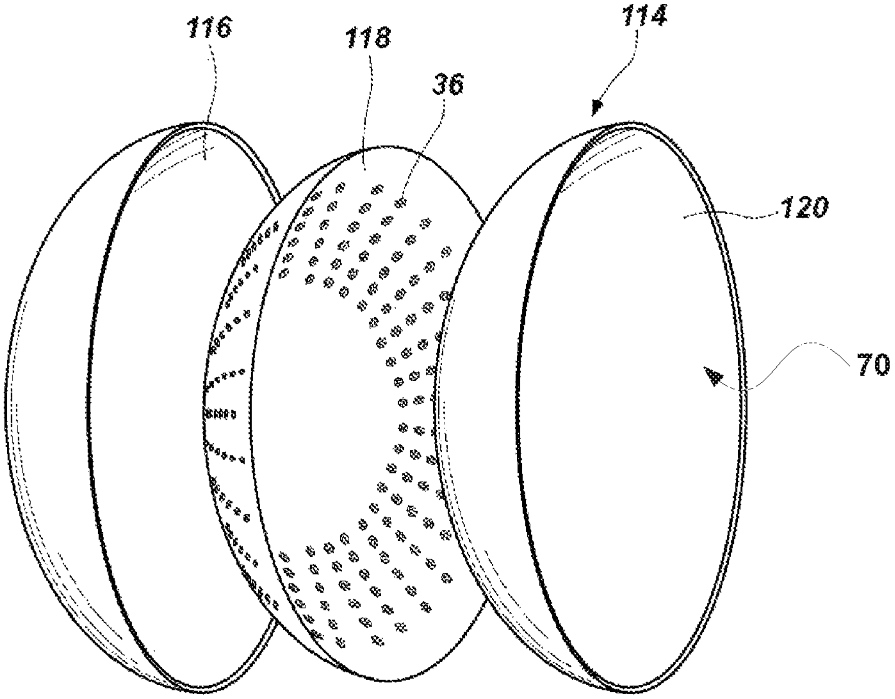
FIG. 22 is an exploded perspective view of an exemplary embodiment of multiple layers of a lens body with features for directing light towards a periphery of a retina, according to the principles of the present disclosure.

FIG. 22 is an exploded perspective view of multiple layers of a composite lens body 114 with features 36 for directing light towards a periphery of a retina according to the principles of the present disclosure. In this example, the lens body 114 includes an anterior layer 116, an intermediate layer 118, and a posterior layer 120. The intermediate layer 118 may include the features 36 for redirecting the light. Such features 36 may be deposited on or integrally formed with the intermediate layer 118. Each of the layers 116, 118, 120 may be cross-linked together. In some examples, the intermediate layer 118 may include a color enhancing material that may or may not make up the features 36 to causes the eye to have a different appearance, such as an apparent change of the color of the iris.

According to one exemplary embodiment, the anterior layer 116 can be formed using any suitable contact lens manufacturing processes including, but in no way limited to, spin casting, cast molding, and/or turning. In one embodiment, the first lens layer is formed using a mold and spinning and curing techniques. A portion of liquid polymeric material is poured into the mold, spun, and cured to form the first lens layer. The spinning and curing steps can be partial so that the first lens layer is not fully cured prior to the insertion of the intermediate layer.

The mold used to form the first lens layer can be any mold suitable for use in the formation of contact lenses. In one embodiment, the mold is laser etched to impart desired optical properties to the final contact lens. The mold can be designed and shaped in any of variety of ways to achieve the desired optical properties for the final contact lens product. Additionally, the amount of liquid polymeric material poured into the mold is generally not limited and can be adjusted based on the desired final properties of the contact lens, including physical properties such as thickness and various optical properties.

The polymeric material used to form the anterior layer 116 can be any of the materials described above. In one embodiment, the polymeric material used to form the first lens layer is at least substantially entirely hydrogel polymers such as HEMA-GMA. In another embodiment, the polymeric material can include a silicone hydrogel material.

The spinning and curing steps can be varied during the formation of the anterior layer 116 based on the desired properties of the final contact lens. For example, it is generally desirable to cure the first lens layer sufficiently to allow it to support the intermediate layer 118 and the posterior layer 120, but not so much that it cannot adequately bond to the intermediate and posterior layers when added.

In one exemplary embodiment, the intermediate layer 118 is formed separately, including the desired features 36, and inserted into the mold onto the anterior layer 116. According to this exemplary embodiment, the intermediate layer 118 is positioned adjacent to the anterior layer 116, followed by the inclusion of additional polymeric material and subsequent spinning and curing to form the posterior layer 120. Alternatively, after a partial cure, the desired features 36 could be formed into the hack of the partially cured anterior layer 116 in situ, followed by a secondary dosing of polymeric material and formation of the posterior layer 120. The features may be formed on the back surface of the anterior layer 116 using any number of forming methods including, but in no way limited to, stamping, etching, material additive processes, or any printing methods that are suitable for use in printing on contact lenses such as pad printing, tamp printing, plate printing, etch printing, dot matrix printing, liquid jet printing, dye sublimation and carrier sheet (laser printing), and printing photosensitive elements that receive subsequent laser treatment.

In one embodiment, the same mold is used for forming the anterior layer 116, the intermediate layer 118, and the posterior layer 120. Alternatively, a separate mold can be used to form one or more layer. The mold can be any mold suitable for use in the formation of a contact lens.

Figure 23:
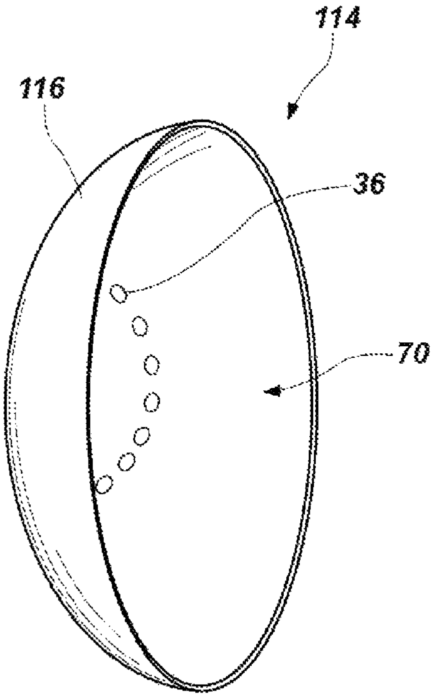
FIG. 23 is a perspective view of an embodiment of a layer of a lens body with features for directing light towards a periphery of a retina, according to the principles of the present disclosure.

FIG. 23 is a perspective view of an assembled composite contact lens including an anterior layer 116 of a lens body 114 with features 36 for directing light towards a periphery of a retina according to the principles of the present disclosure. In this example, the layer 116 includes features that are incorporated on a posterior surface 70 of the anterior layer 116 after printing, embossing, or stamping. In such an example, a posterior layer 120 may be bonded to the anterior layer 116. In other examples, a posterior layer 120 may have the features 36 formed on an anterior surface 38, and an anterior layer 116 may be positioned over the anterior surface 38 of the posterior layer 120 such that features 36 are between the anterior layer 116 and the posterior layer 120.

Figure 24:
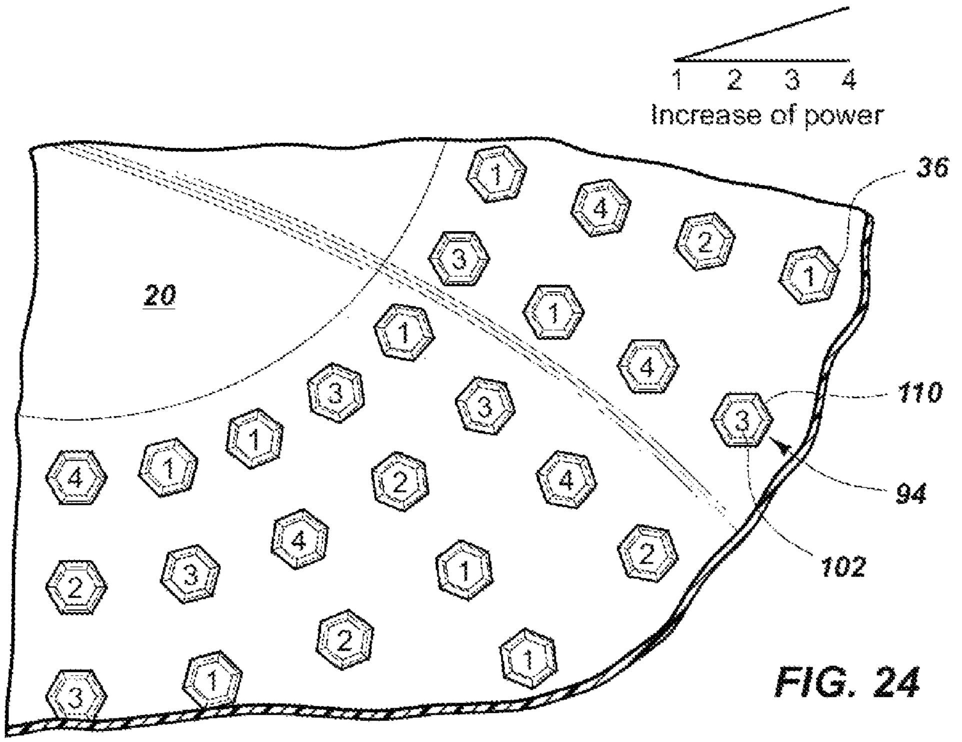
FIG. 24 is a perspective view of a portion of a lens body including features of varying powers, according to the principles of the present disclosure.
Figure 25:
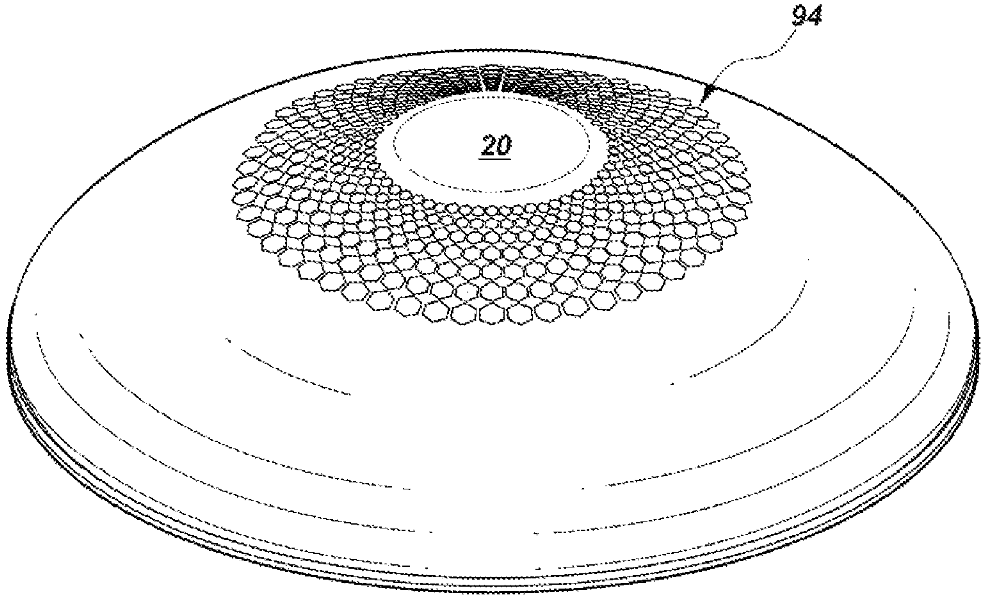
FIG. 25 is a perspective view of the entire lens body including features of varying powers, according to the principles of the present disclosure.
Figure 26:
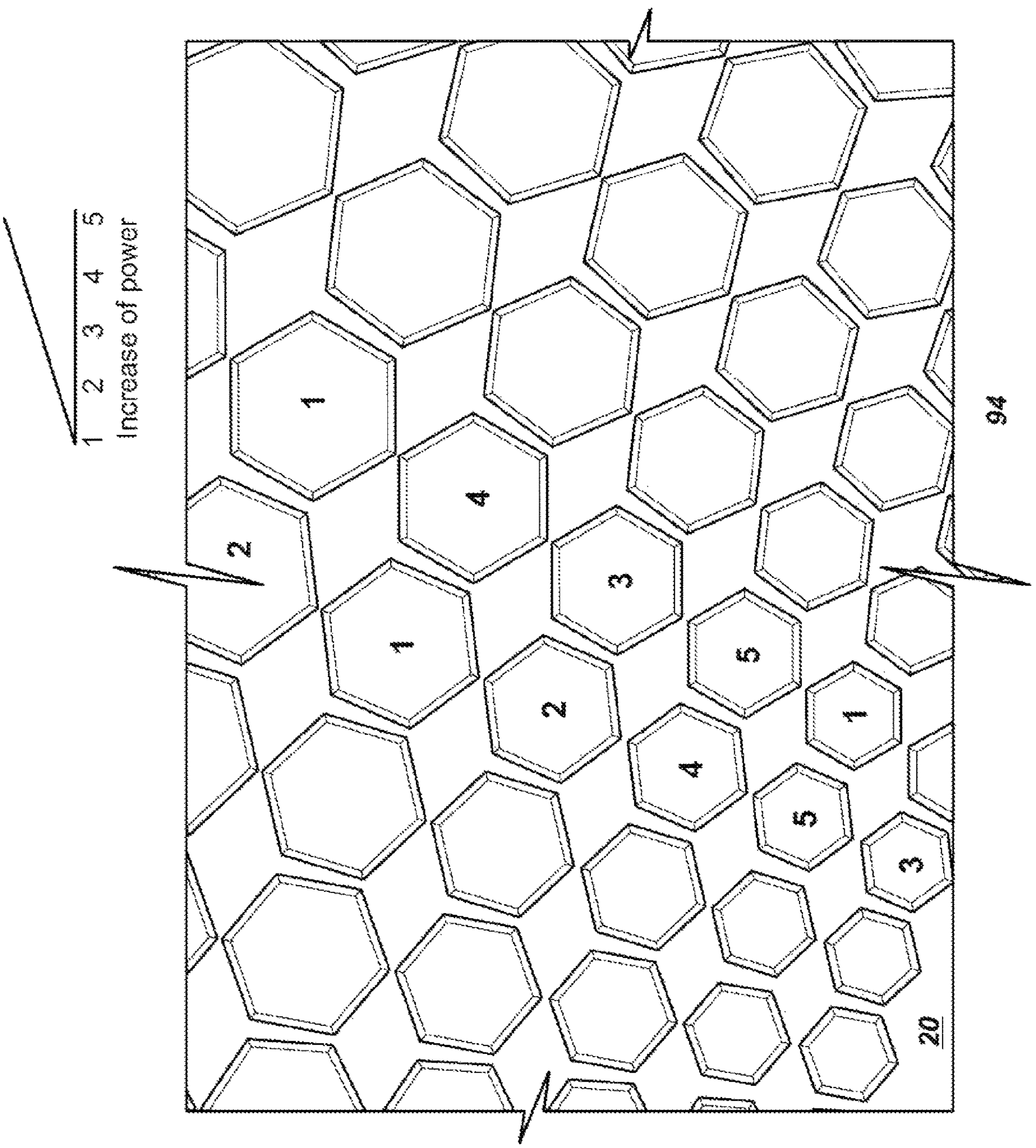
FIG. 26 is a close up view of an array of features having varying powers, according to the principles of the present disclosure.

FIGS. 24-26 illustrate the design flexibility that can be accomplished by incorporating an intermediate layer in a composite lens. As illustrated in FIG. 24, a plurality of lenslet features 36 having, for example, a hexagonal shape 94, including a central face 102 and side faces 100, are formed in the non-optic region of an intermediate layer of a composite lens. As illustrated, the use of precision tool making methodologies, such as 3-D nano-printing and nano-lithography, allows for precise design and sequencing of the lenslet features 36 on the intermediate layer. As illustrated in FIG. 24, the lenslet features 36 have varying powers ranging from 1-4. According to one exemplary embodiment, the zones of powers exhibited by the lenslet features 36 can be random within a prescribed range of powers, or sequentially designed for a specifically desired effect. FIG. 25 is a perspective view of the entire lens body including an intermediate layer having lenslet features 36 having varying powers, according to the principles of the present disclosure. Similarly, FIG. 26 illustrates a more compact grouping of lenslet features 36 assuming a hexagonal shape 94. As illustrated in FIG. 26, the present system and method provides a high level of precision and flexibility when designing a lens for a desired treatment.

Figure 27:
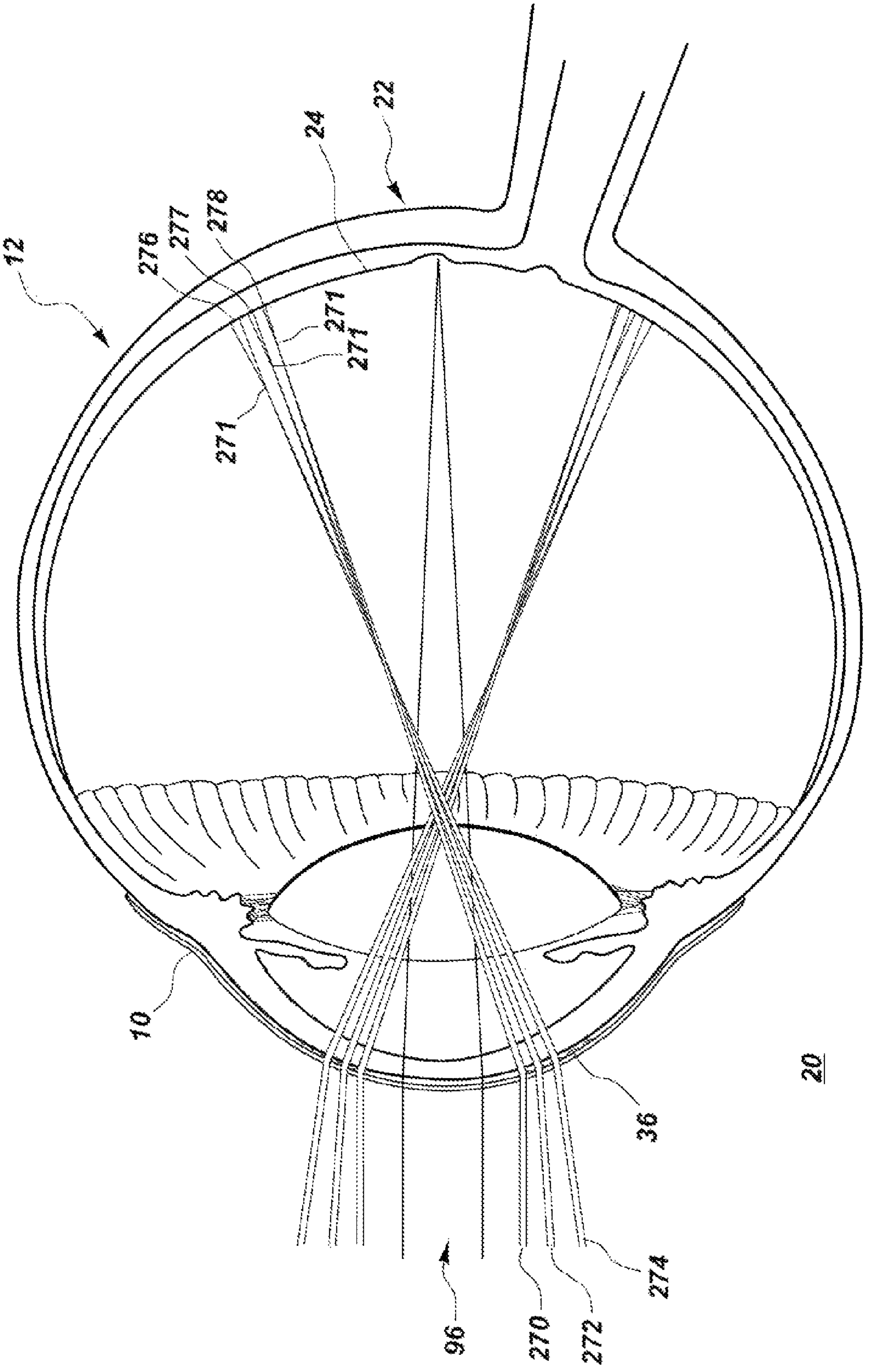
FIG. 27 is a cross-sectional view of a an ocular lens directing light with varying focal points into an eye, according to the principles of the present disclosure.

FIG. 27 is a cross-sectional view of a an ocular lens directing light with varying focal points and intensities into an eye according to the principles of the present disclosure. As illustrated in FIG. 27, the use of the high precision manufacturing techniques and the hexagonal lenslet features 36, different light focal points and intensities can be generated by a single lens. As shown, an ocular lens 10 including a plurality of hexagonal lenslet features 36 can direct light having different focal points 271 to the peripheral region of the retina. As shown, the ocular lens 10 is configured to properly focus the central light 96 passing through the optic zone of the lens to the central region 22 of the retina 24 to provide clear distance vision. Additionally, the parallel light 270 and peripheral light 272 passes through the hexagonal lenslet features 36 and onto the peripheral region of the retina. By varying the focal point of the various hexagonal lenslet features 36, different light intensities 276, 277, 278 reach the peripheral region of the retina. Consequently, the optical lens can induce a desired and varying stimulus to the peripheral region of the retina.

Figure 28:
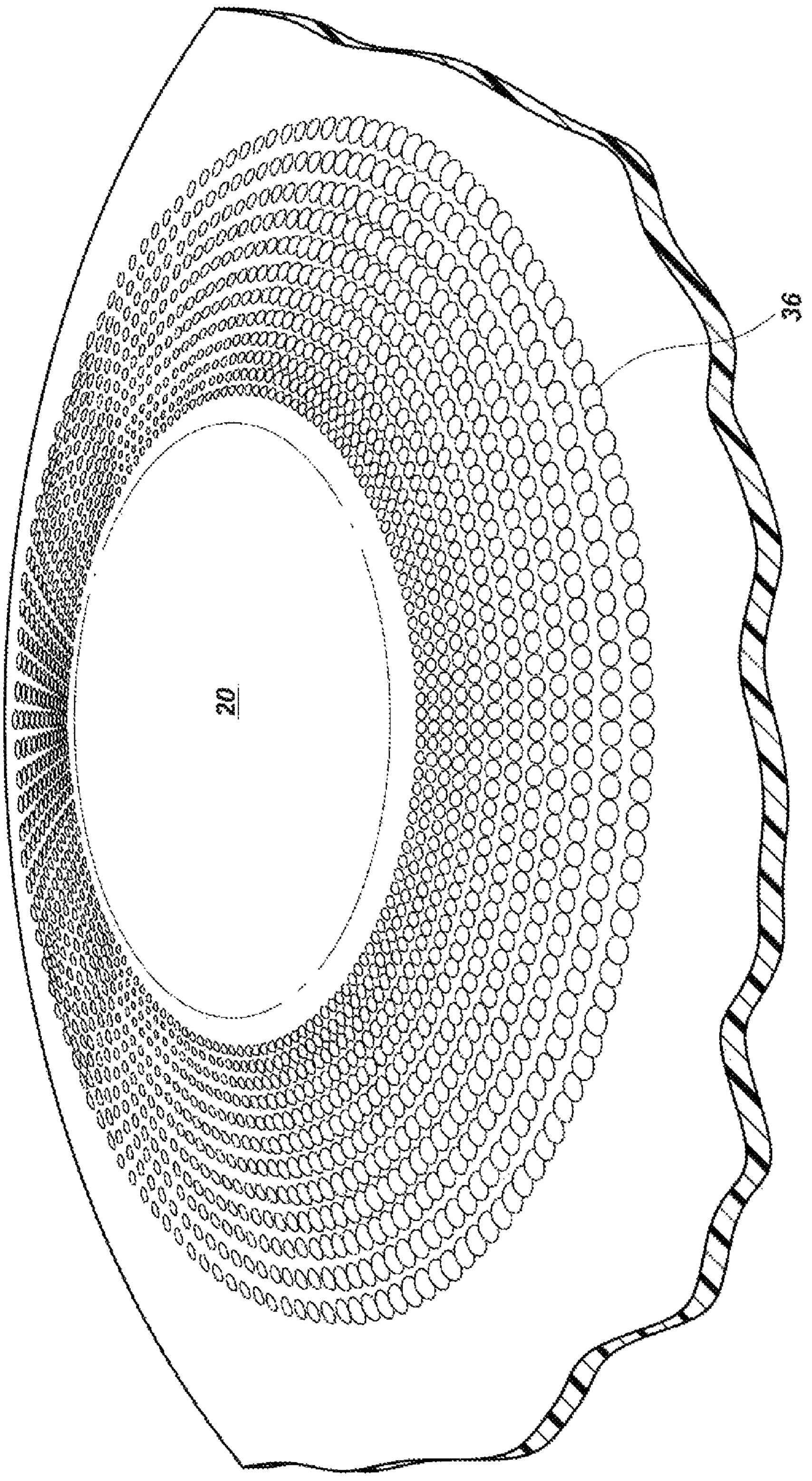
FIG. 28 is a lens body including a plurality of semi-sphere lenslets formed on a lens body, according to the principles of the present disclosure.

While the above-mentioned intermediate lens is described as having hexagonal shaped lenslet features 36 for the selective focusing of peripheral light, any number of lens and lenslet geometries may be used according to the present exemplary system and method. As illustrated in FIG. 28, a lens body may include a plurality of semi sphere lenslet features 36 formed on the anterior surface of the ocular lens 10. As mentioned above, the anterior surface of the ocular lens 10 can be selectively modified to include such lenslets via precision molding of the spin cast lens mold. According to one exemplary embodiment the lenslet features 36 are designed such that they have a similar power and prism to form a pseudo vision she'll anterior to the retina. Alternatively, the lenslet features 36 may have different power and prism to selectively vary the light intensities that reach the peripheral region of the retina.

Figure 29:
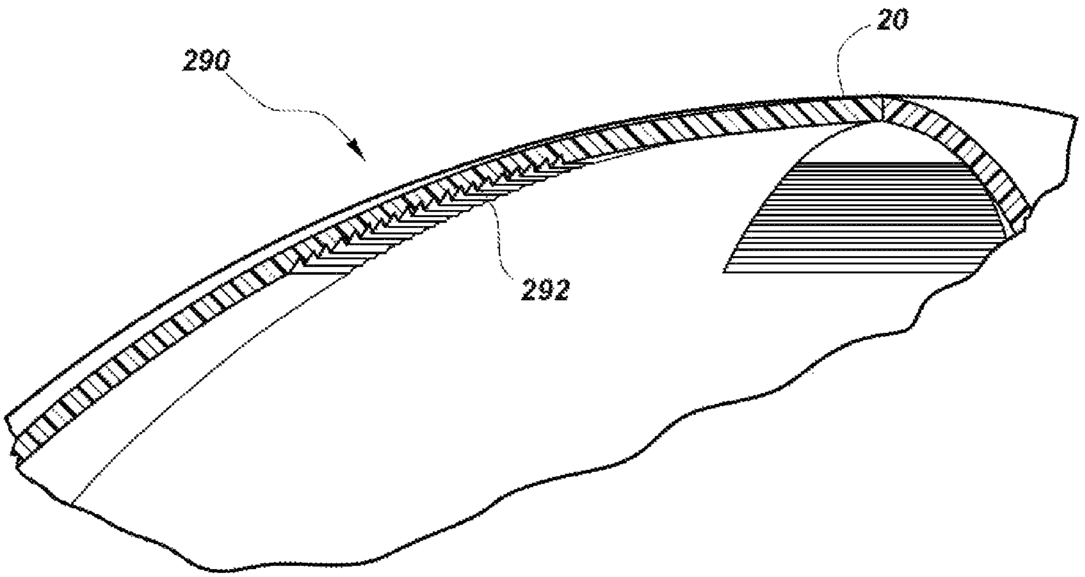
FIG. 29 is a cross-sectional view of a portion of a lens body including Fresnel type sections, according to the principles of the present disclosure.
Figure 30:
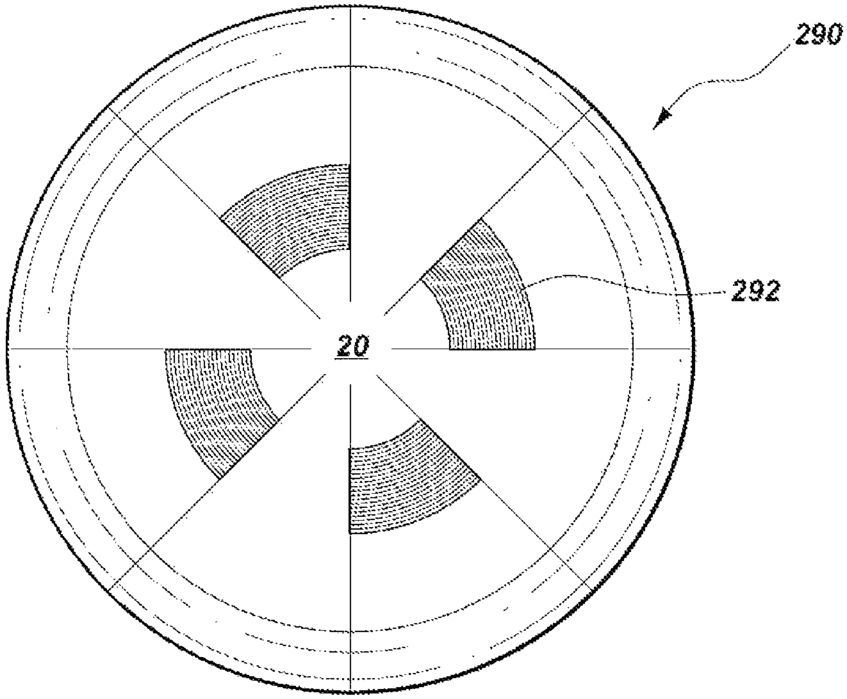
FIG. 30 is a back view of an inner Fresnel type lens, according to the principles of the present disclosure.
Figure 31:
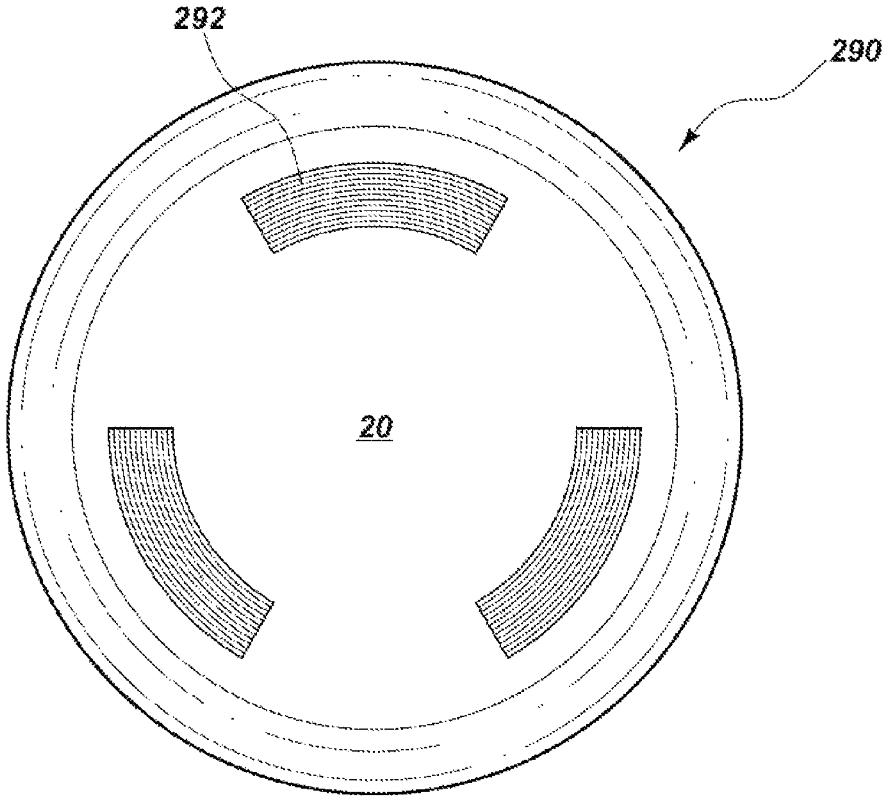
FIG. 31 is a back view of an inner Fresnel type toric lens, according to the principles of the present disclosure.

Alternatively, Fresnel type sections may be used to selectively direct peripheral light to the peripheral region of the retina. As illustrated in FIGS. 29-31, a Fresnel type lens 290 includes at least one layer of the ocular lens 10 having Fresnel prisms 292 formed therein. According to one exemplary embodiment, the use of Fresnel prisms 292 allows for the manufacture of ocular lenses that will redirect peripheral light as noted above, with reduced mass and volume of material.

FIG. 30 is a back view of an inner Fresnel type lens, according to the principles of the present disclosure. As illustrated, the Fresnel type lens 290 may be configured to properly focus the central light 96 passing through the optic zone 20 of the lens to the central region 22 of the retina 24 to provide clear distance vision. Additionally a number of Fresnel prisms 292 may be formed outside the central optic zone 20 in the non-optic region 92 of the ocular lens 10. According to the illustrated embodiment, the lens is divided into octants with alternating octants containing a Fresnel prisms 292. Accordingly, the Fresnel prisms 292 may be designed to impart high levels of desired and varying stimulus to the peripheral region of the retina.

Similarly, the present exemplary systems and methods may be incorporated into toric lenses. For example, FIG. 31 is a back view of an inner Fresnel type toric lens, according to the principles of the present disclosure. As illustrated, the inner Fresnel prisms 292 are disposed in thirds corresponding to the standard orientation of a toric lens.

While, the examples above have been described with reference to specific types of ocular lens, feature shapes, feature material, layers, and other parameters, any appropriate type of parameter may be incorporated into the lens in accordance with the principles of the present disclosure. Thus, any number of features, shapes, or layers may be used in accordance with the principles described herein. Further, multiple types of materials with differing optical refractive characteristics may be used to make the features. Further, the features may be made with different material to achieve optimal bonding, spacing, adhesion, optics, or other types of characteristics.

The terms recited in the claims should be given their ordinary and customary meaning as determined by reference to relevant entries in widely used general dictionaries and/or relevant technical dictionaries, commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used in a manner that is more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure the term shall mean," etc.).

References to specific examples, use of "i.e.," use of the word "invention," etc., are not meant to invoke exception (b) or otherwise restrict the scope of the recited claim terms. Other than situations where exception (b) applies, nothing contained herein should be considered a disclaimer or disavowal of claim scope.

The subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be given their broadest interpretation in view of the prior art and the meaning of the claim terms.

As used herein, spatial or directional terms, such as "left," "right," "front," "back," and the like, relate to the subject matter as it is shown in the drawings. However, it is to be understood that the described subject matter may assume various alternative orientations and, accordingly, such terms are not to be considered as limiting.

Articles such as "the," "a," and "an" can connote the singular or plural. Also, the word "or" when used without a preceding "either" (or other similar language indicating that "or" is unequivocally meant to be exclusive—e.g., only one of x or y, etc.) shall be interpreted to be inclusive (e.g., "x or y" means one or both x or y).

The term "and/or" shall also be interpreted to be inclusive (e.g., "x and/or y" means one or both x or y). In situations where "and/or" or "or" are used as a conjunction for a group of three or more items, the group should be interpreted to include one item alone, all of the items together, or any combination or number of the items. Moreover, terms used in the specification and claims such as have, having, include, and including should be construed to be synonymous with the terms comprise and comprising.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be consumed in light of the number of recited significant digits and by applying ordinary rounding techniques.

All ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

What is claimed is:

1. A method of making an ocular lens, comprising:

forming a spin casting mold with a lens mating surface by molding a profile on a first side of a mold material where the profile contains at least one recess, which forms at least one feature on the ocular lens configured to direct peripheral light into an eye away from a central region of a retina of the eye when worn on the eye, wherein the feature further causes the peripheral light directed away from the central region of the retina to be directed towards a peripheral region of the retina;

applying a liquid lens material to the first side of the spin casting mold;

spinning the spin casting mold; and at least partially curing the liquid lens material to form the ocular lens comprising the at least one feature, wherein at least partially curing the liquid lens material comprises curing the liquid lens material at least to a point where the liquid lens material retains its shape.

2. The method of claim 1, wherein the at least one feature is located outside of an optic zone of the ocular lens.

3. The method of claim 1, wherein at least partially curing the liquid lens material includes exposing the liquid lens material to actinic radiation.

4. The method of claim 1, wherein the at least one feature is configured to control an axial growth rate of an eye when worn by a user.

5. The method of claim 4, wherein the step of forming a spin casting mold with a lens mating surface further comprises manufacturing injection mold tooling corresponding to a surface of the ocular lens, including the at least one feature;

wherein the injection mold tooling is manufactured with one of a 3-D nano-printing, a nano-lithography process, precision lathing, 5-axis milling, or fused deposition.

6. The method of claim 4, wherein the at least one feature is configured to focus light in front of the peripheral region of the retina when worn on the eye.

7. The method of claim 4, wherein the at least one feature is configured to focus light behind the peripheral region of the retina when worn on the eye.

8. The method of claim 4, wherein the at least one feature is configured to modify a development of myopia.

9. The method of claim 4, wherein the at least one feature is configured to prevent a development of myopia.

10. A method of making an ocular lens, comprising:

forming a plurality of optical features on at least one surface of the ocular lens;

wherein:

the ocular lens comprises an optic zone shaped to direct central light towards a central focal point of a central region of a retina when worn on an eye of a user;

the optical features direct peripheral light into the eye away from the central region of the retina; and each of the optical features are noncontiguous with one another.

11. The method of claim 10, wherein forming the optical features includes printing an optical material onto the at least one surface of the ocular lens.

12. The method of claim 11, wherein printing the optical material onto the at least one surface of the ocular lens includes using a pad printing process, a plate printing process, a etch printing process, a dot matrix printing process, a laser printing process, a tamp printing process, a liquid jet printing process, or combinations thereof.

13. The method of claim 10, wherein forming the optical features comprises selectively depositing an optical material on an anterior surface of the ocular lens.

14. The method of claim 10, wherein forming the optical features comprises selectively depositing an optical material on an internal surface of at least one layer of a plurality of layers forming a lens body.

15. The method of claim 14, wherein the at least one layer is an intermediate layer.

16. The method of claim 15, further comprising:

inserting the intermediate layer between a posterior layer shaped to contact the eye and an anterior layer; and cross linking the posterior layer and the anterior layer together to form a bonded lens body.

17. The method of claim 10, wherein forming the optical features comprises:

forming a composite optical lens having at least an anterior layer, and intermediate layer and a posterior layer, including:

molding an intermediate layer including the optical features; and bonding the intermediate layer to the anterior layer and the posterior layer.

18. The method of claim 10, wherein an optical material of the optical features comprises a different refractive index than a material of the optic zone.

19. The method of claim 10, wherein an optical material of the optical features comprises the same refractive index as a material of the optic zone.

20. The method of claim 10, wherein an optical material of the optical features comprises a silicone material.

21. The method of claim 10, wherein an optical material of the optical features comprises a hydrogel material.

* * * * *